(12) United States Patent
Miwa et al.

(10) Patent No.: US 7,399,284 B2
(45) Date of Patent: Jul. 15, 2008

(54) ULTRASONIC IRRADIATION APPARATUS

(75) Inventors: Hirohide Miwa, Kawasaki (JP); Hiroaki Miwa, Kawasaki (JP); Masato Kino, Setagaya-ku (JP)

(73) Assignee: Miwa Science Laboratory Inc., Kanagawa (JP)

( * ) Notice: Subject to any disclaimer, the term of this patent is extended or adjusted under 35 U.S.C. 154(b) by 552 days.

(21) Appl. No.: 10/296,039

(22) PCT Filed: May 22, 2001

(86) PCT No.: PCT/JP01/04265

§ 371 (c)(1),
(2), (4) Date: Nov. 21, 2002

(87) PCT Pub. No.: WO01/89723

PCT Pub. Date: Nov. 29, 2001

(65) Prior Publication Data
US 2003/0135135 A1 Jul. 17, 2003

(30) Foreign Application Priority Data
May 22, 2000 (JP) ............... 2000-149135

(51) Int. Cl.
*A61H 1/00* (2006.01)
*A61H 1/02* (2006.01)
*A61H 5/00* (2006.01)

(52) U.S. Cl. .................................. 601/2; 600/439

(58) Field of Classification Search ................. 600/128, 600/439, 437; 601/2, 3
See application file for complete search history.

(56) References Cited

U.S. PATENT DOCUMENTS 3,552,382 A * 1/1971 Mount ..................... 600/453

(Continued)

FOREIGN PATENT DOCUMENTS

EP 0 181 506 5/1986

(Continued)

*Primary Examiner*—Brian Casler
*Assistant Examiner*—Jacqueline Cheng
(74) *Attorney, Agent, or Firm*—Paul A. Guss

(57) ABSTRACT

An ultrasonic irradiation apparatus irradiates ultrasonic waves onto a wide area having three-dimensionally curved surfaces. An ultrasonic irradiator having a plurality of ultrasonic transducer is arranged in a plane. The position of at least a portion of the ultrasonic transducers is mutually and flexibly changeable in three dimensions. Ultrasonic transducers are installed on a surface of a flexible and/or elastic sheet member or net member. The ultrasonic irradiator may include a plurality of ultrasonic transducers formed on a flexible piezoelectric sheet member, including driving electrodes arranged on one surface and opposed electrodes arranged on another surface. The ultrasonic irradiator may be installed on or inside of a flexible planar bag containing a fluidic ultrasonic conductive medium. A mechanism is provided for moving or tilting the ultrasonic irradiator with respect to the object, or a band-holding member may be provided for fitting the irradiator to the object.

12 Claims, 11 Drawing Sheets

U.S. PATENT DOCUMENTS

| | | | | |
|---|---|---|---|---|
| 3,603,921 | A | * | 9/1971 | Dreisbach .................... 367/155 |
| 3,964,014 | A | * | 6/1976 | Tehon ........................ 367/155 |
| 4,276,491 | A | * | 6/1981 | Daniel ........................ 310/317 |
| 4,446,395 | A | * | 5/1984 | Hadjicostis ................. 310/327 |
| 4,483,343 | A | * | 11/1984 | Beyer et al. ................. 600/437 |
| 4,848,139 | A | * | 7/1989 | Blake-Coleman et al. .. 73/61.75 |
| 4,965,532 | A | * | 10/1990 | Sakurai ......................... 331/4 |
| 5,078,143 | A | * | 1/1992 | Okazaki et al. ............. 600/439 |
| 5,078,144 | A | * | 1/1992 | Sekino et al. ............... 600/439 |
| 5,298,602 | A | * | 3/1994 | Shikinami et al. ........... 528/361 |
| 5,619,999 | A | * | 4/1997 | Von Behren et al. ........ 600/445 |
| 5,792,058 | A | * | 8/1998 | Lee et al. .................... 600/459 |
| 5,810,009 | A | * | 9/1998 | Mine et al. .................. 600/459 |
| 5,897,495 | A | * | 4/1999 | Aida et al. .................. 600/411 |
| 6,007,499 | A | * | 12/1999 | Martin et al. .................. 601/3 |
| 6,023,632 | A | * | 2/2000 | Wilk .......................... 600/407 |
| 6,575,956 | B1 | * | 6/2003 | Brisken et al. .............. 604/500 |

FOREIGN PATENT DOCUMENTS

| | | |
|---|---|---|
| EP | 181506 A2 * | 5/1986 |
| EP | 0 420 190 | 4/1991 |
| GB | 2 282 931 | 4/1995 |
| WO | WO 99/48621 | 9/1999 |
| WO | WO 9948621 A2 * | 9/1999 |

\* cited by examiner

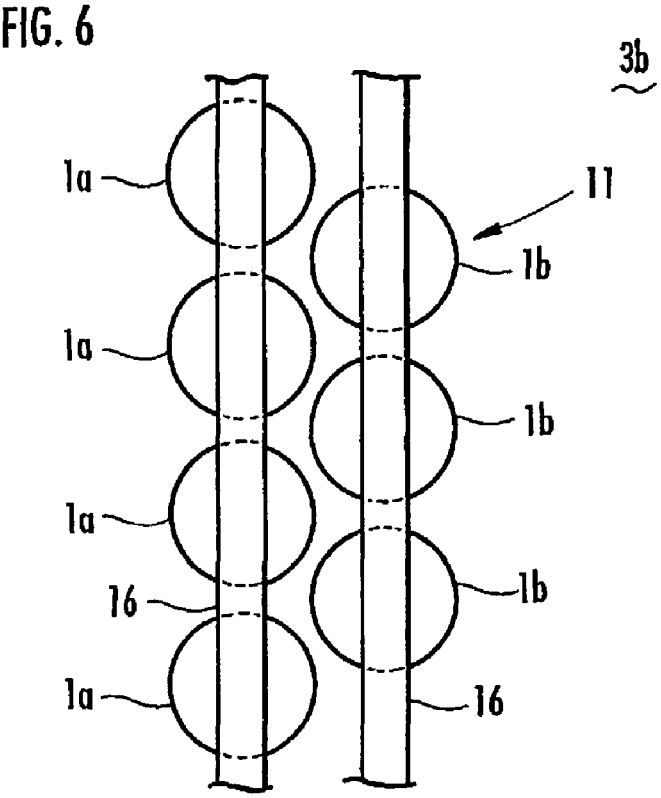
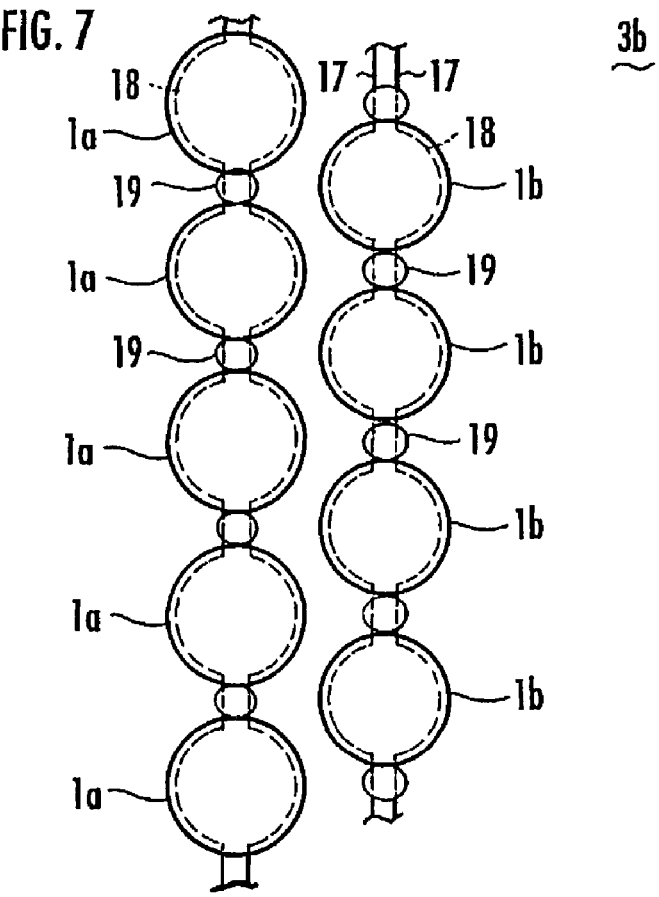

ULTRASONIC IRRADIATION APPARATUS

CROSS-REFERENCE TO RELATED APPLICATION

This application is the U.S. national phase of PCT application number PCT/US01/16929, filed May 24, 2001, which further claims priority to U.S. patent application Ser. No. 09/578,024, filed May 24, 2000.

TECHNOLOGICAL FIELD

The present invention relates to an ultrasonic irradiation apparatus for irradiating, with ultrasonic waves, a wide area of an object to be irradiated such as a living body.

BACKGROUND ART

The inventor of the present invention conducted research and discovered that fats within a living body were decomposed (lipolysis) by irradiating the living body with ultrasonic waves having a specific frequency. A patent application regarding an ultrasonic wave irradiation apparatus was filed and published as PCT Publication Number WO 99/39677 on Aug. 12, 1999.

In the practice of the previous invention, it was required to irradiate the living body with ultrasonic waves. The living body has wide three-dimensionally curved surfaces composed of complicated uneven surfaces such as, e.g., the abdominal region, the thighs, the buttocks or the chin. Therefore, it is difficult to evenly irradiate the surface of a living body with ultrasonic waves.

To solve such a problem, in the published international patent application, there was disclosed:

(1) an apparatus, having an ultrasonic transducer arranged on a side wall of a bath tub, for irradiating a living body via hot water in the bath tub with ultrasonic waves generated by the ultrasonic transducer;

(2) an apparatus, having an ultrasonic transducer arranged on the bottom of a water chamber having an upper side thereof left open, for irradiating, with ultrasonic waves, a living body contacting the water on the upper opening area via the water in the water chamber; and (3) an apparatus, having an ultrasonic transducer arranged within a shower head, for irradiating, with ultrasonic waves, a living body via water or hot water flowing out from the shower head.

It has been known to irradiate with ultrasonic waves for, e.g., enhancing beauty, acceleration of blood circulation and for curing stiffness in the shoulder or lumbago, and some conventional ultrasonic irradiation apparatuses have been known for these purposes. The conventional ultrasonic irradiation apparatus has a single ultrasonic transducer having a diameter of about 20 to 50 mm, and irradiation, with ultrasonic waves, over a desired wide area of a living body is performed by scanning the living body surface with an acoustic output part of the apparatus.

In the conventional ultrasonic irradiation apparatus, ultrasonically irradiating the living body having three-dimensionally curved surfaces is easily conducted without large size equipment such as a bath tub, a water chamber or a shower system, because scanning can cover the living body surface to some extent. But, when the scanning area becomes wider, in the conventional system it requires a long time to scan wider areas because of the time required to manually scan the single ultrasonic transducer to accumulate the necessary irradiation dose (intensity of irradiation×the accumulated time of irradiation) per unit surface area. Hence, the work load for an operator, such as a doctor, becomes heavier.

In the published international patent application, an apparatus has been disclosed, having a single ultrasonic transducer and an acoustic lens arranged in front of the ultrasonic transducer, for irradiating a living body with ultrasonic waves through a bag containing an ultrasonic conducting medium such as, e.g., water or jelly. In the system of the published patent application, it is possible not only to make close contact with a living body via the water bag, but also to expand the area of irradiation greater than using a sole ultrasonic transducer, due to a function of the acoustic lens, and thereby one is able to effectively scan the living body.

However, in the case where the area to be scanned is wider, the system disclosed in the published international patent application has the same problems as the conventional ultrasonic irradiation apparatus. In other words, it takes a long time to scan wider areas and the load imposed on the operator becomes heavier.

Further, in the apparatus for irradiating ultrasonic waves via a bag containing an ultrasonic conducting medium, the distance between the acoustic lens and a window portion of the bag, which outputs ultrasonic waves and which is in contact with the living body, must become longer to make the irradiation area wider, and thus the amount of water is increased. As the result, the pressure of the water weight is transferred to the living body, and it is difficult to make adjustments so as to partially support and lessen the pressure due to such weight. Further, in the apparatus for irradiating with ultrasonic waves via the bag containing the ultrasonic conducting medium, the position of the living body to be irradiated with ultrasonic waves is limited because, if the irradiation direction to the living body is not vertical, the output window of the bag is greatly deformed by gravity and thereby it is difficult to scan smoothly.

DISCLOSURE OF THE INVENTION

An object of the present invention is to provide an apparatus capable of easily irradiating, with ultrasonic waves, a wide area of an object having three-dimensional surfaces.

To accomplish the above object, an ultrasonic irradiation apparatus according to the present invention comprises an ultrasonic irradiator including a plurality of ultrasonic transducers arranged in a planar pattern wherein at least a portion of the ultrasonic transducers are mutually and flexibly deformable in three dimensions. In the present patent application, the term of "flexibly deformable in three dimensions" also includes the meaning of "flexibly deformable in two dimensions."

In the ultrasonic irradiation apparatus according to the present invention, an area within the object, where ultrasonic waves can be irradiated at one time, becomes considerably wider than in the conventional apparatus having a single ultrasonic transducer, because the plurality of ultrasonic transducers are arranged in a planar pattern. Thus, the load imposed on the operator can be reduced when irradiating a wide area of the object with ultrasonic waves.

Further, in the ultrasonic irradiation apparatus according to the present invention, at least a portion of the plurality of ultrasonic transducers arranged in the planar configuration are mutually deformable in three dimensions. As a result, the ultrasonic transducers can be fitted along the surface of the object having three-dimensionally curved surfaces, such as a living body, and the object can be evenly irradiated with ultrasonic waves.

The ultrasonic irradiation apparatus according to the present invention is characterized in that the plurality of ultrasonic transducers are arranged on a flexible and/or elastic sheet member, so as to be mutually deformable in three dimensions. As examples of the flexible and/or elastic sheet member, several types of rubber sheet members, foamed rubber sheet members, such as expanded butylene or expanded silicon, fabrics or unwoven textiles may be applicable.

A sheet member having elasticity is preferable, although one having only flexibility may be used. In the case where the sheet member has only flexibility, the sheet member should have good flexibility in one direction, but the sheet member should be difficult to be deformed in a direction transverse to the direction which is deformed first.

Therefore, it is preferable that the sheet member has a plurality of linear recesses (this word is used interchangeable with the term "slot" hereafter) so that the sheet member is flexibly deformed based on both edges of the linear recesses becoming apart from each other. Thereby, when the sheet member is deformed in a direction along the linear recesses, the sheet can be also deformed in a direction transverse to the linear recesses, and the position of the ultrasonic transducers can be mutually deformed in three dimensions. The shape and width of the linear recesses may be freely determined.

The linear recesses should be formed from one surface toward the other surface in the sheet member, and may or may not penetrate though to the other surface.

Further, the ultrasonic irradiation apparatus according to the present invention is characterized in that the plurality of ultrasonic transducers are arranged on a net member having flexibility and/or strechability, so that the position of the plurality of ultrasonic transducers is mutually deformable in three dimensions. As the flexible net member, a material is used that is composed of at least one type of material selected from a string, a band, a spring, a chain, and rods that are linked so as to be mutually rotatable.

Further, the ultrasonic irradiation apparatus according to the present invention is characterized in that the plurality of ultrasonic transducers making up the ultrasonic irradiator are composed of driving electrodes arranged on one surface of a flexible piezoelectric sheet member and opposed electrodes arranged on the other surface of the flexible piezoelectric sheet member, facing each other. Hence, the position in the plurality of ultrasonic transducers is mutually deformable in three dimensions. As the flexible piezoelectric sheet member, a sheet member composed of an organic piezoelectric material such as polyvinylidene fluoride (PVDF), or a sheet member composed of a plastic material kneaded with piezoelectric particulates, comprising ceramics such as $Pb(Zr*Ti_3)O_3$ (PZT), can be used.

The flexible piezoelectric material has a characteristic of good flexibility in one direction, but when the flexible piezoelectric material is deformed in the one direction, the flexible piezoelectric material is difficult to be deformed in a direction transverse to the deformed direction. Therefore, it is preferable that the flexible organic piezoelectric material has a plurality of linear recesses and is flexibly deformable based on the edges of the linear recesses moving apart from each other. Thereby, when the flexible organic piezoelectric material is deformed in a direction along the linear recesses, the material can also be deformed in a direction crossing the linear recesses, and the position of the ultrasonic transducers can be mutually deformed in three dimensions. The shape and width of the linear recesses may be freely determined.

The linear recesses should be formed from one surface toward the other surface in the piezoelectric material, and may or may not penetrate the piezoelectric material through to the other surface.

In any one of the ultrasonic irradiators described above, it is preferable that a soft material layer or a fluidic material layer, which is composed of an ultrasonic conducting medium for transferring ultrasonic waves to an object to be irradiated, be arranged between the ultrasonic irradiator and the object. Thereby, an additional function, such as optional setting of temperature, can be achieved with the soft material layer or the fluidic material layer.

It is preferable, in the ultrasonic irradiator in which a plurality of ultrasonic transducers are arranged in a plane, or in any of the ultrasonic irradiators described above, that said transducers be arranged on the surface of a planar bag which has a fluidic material serving as an ultrasonic conducting medium and which has flexibility. Thereby, the ultrasonic irradiator and the planar bag can be integrated, and handling becomes easier.

Such a bag is deformable because the bag itself is flexible and contains the fluidic material therein. However, it is applicable further to arrange a tube, channeling the outside of the bag and the inside of the bag, and a pump for changing a volume of the fluidic material in the bag over time, by adding/reducing the fluidic material through the tube. Thereby, the shape of the bag can be intentionally deformed.

In the case where an output plane (window) of ultrasonic waves of the bag is applied vertically to a living body, an offset of the output plane due to blisters or inferior contact between the bag and the living body may be caused, because the fluidic material is pulled down toward a bottom portion of the bag due to gravity and the like. Therefore, it is preferable that the bag has a connection member for connecting an internal upper plane and an internal bottom plane in the bag, and for maintaining a maximum distance between the internal upper plane and the internal bottom plane at least within a predetermined range.

In the ultrasonic irradiation apparatus according to the present invention, a plurality of ultrasonic transducers being arranged in plane, or any one of the ultrasonic irradiators described above may be arranged on the inside of a flexible planar bag having at least one flexible surface (window), and containing a fluidic material as the ultrasonic conducting medium, for averaging a local intensity variation caused by interference between the ultrasonic waves mainly of the adjacent transducers overlapping within the object, while irradiating the object having three-dimensionally curved surfaces, and also averaging an uneven spatial distribution of the sonic field caused by the arrangement of the ultrasonic transducers. The flexible planar bag may also have elasticity. Then, in the ultrasonic irradiation apparatus according to the present invention, it is preferable that at least one surface of the ultrasonic irradiator be arranged so as to be easily moved along the plane portion of the flexible planar bag and/or so as to be easily tilted to the plane portion of the flexible planar bag. Because the ultrasonic irradiator is arranged so as to be easily moved and/or tilted as described above, the position of the ultrasonic transducers in the ultrasonic irradiator with respect to an object can be relatively changed. Thereby, it is possible to spatially average any unevenness of the sonic field caused by overlap, as described above, as well as any unevenness caused by the arrangement of the ultrasonic transducers.

The planar bag having at least one flexible plane is easily handled when a back plane opposed to the window plane for outputting ultrasonic waves is made rigid. Also the rigid back can be a base member for moving or tilting the ultrasonic transducers. The planar bag having at least one flexible plane comprises a plurality of straight recesses arranged mutually in parallel on the back plane so as to be flexibly deformable in a direction transverse to the straight linear recesses. Thereby, the planar bag can be deformed in the direction transverse the straight recesses, and with respect to a curved surface along the straight recesses, the flexibility of an output window can adaptively accommodate the curvature. Then, the planar bag having at least one flexible plane can be fitted three-dimensionally with the object. In this case, the weight of the flexible planar bag becomes light because the deformation of the flexible plane, serving as the output window, becomes slight and the thickness of the fluidic material can be kept thin.

In the ultrasonic irradiation apparatus according to the present invention, the soft material or the fluidic material serving as an ultrasonic conducting medium is preferably a hot pack (i.e., a heatable high specific heat material) or a cold pack (i.e., a refrigeratable high specific heat material). The effectiveness of irradiation by ultrasonic waves with respect to the object can be improved by controlling the temperature of the contacting surface of the soft material or the fluidic material, which has been heated or cooled previously. In the case where the object is a human body, the tactile feeling of the object can be improved by previously heating or cooling the soft material or the fluidic material.

The ultrasonic irradiation apparatus according to the present invention is characterized in that the ultrasonic irradiation apparatus has a band-like holding member for fitting the ultrasonic irradiator to the object. Because the ultrasonic irradiation apparatus has such a band holding member, the ultrasonic irradiator can be held and fitted to the object, and the load on the operator can be greatly reduced.

Then, the ultrasonic transducers are preferably arranged so as to be easily moved, reciprocating along a length and/or width direction in the band-like holding member, to average a local variation of the sonic field caused by interference of adjacent ultrasonic transducers, or to average an uneven spatial distribution of the sonic field caused by the arrangement of the ultrasonic transducers at the inside of the object.

The ultrasonic irradiation apparatus according to the present invention is characterized in that the ultrasonic irradiator comprises means for being driven electrically by at least two or more drive systems, each of which drives the plurality of ultrasonic transducers in mutually different electrical conditions. Thus, a spatial distribution of intensity caused by interference at overlapping portions of each sonic field of the ultrasonic transducers is averaged, without being fixed only by a single drive system, while each ultrasonic transducer position is mutually deformed in three dimensions.

In the ultrasonic irradiation apparatus according to the present invention, the ultrasonic irradiator comprises the aforementioned driving means, so that each of the plurality of ultrasonic transducers are driven in mutually different conditions. Hence, the position on which ultrasonic waves from each ultrasonic transducer overlap within the object is constantly changed. Thereby, in the ultrasonic irradiation apparatus according to the present invention, the irradiation dose of ultrasonic waves inside the object is spatially averaged, and an excessive or insufficient dose of irradiation at some specific portion within the object can be avoided.

In the ultrasonic irradiation apparatus according to the present invention, it is preferable that the ultrasonic irradiator comprises an impedance adjusting means for adjusting an output allocation to the plurality of ultrasonic transducers, so that each sonic field of transducers forms a predetermined intensity ratio when each transducer position is mutually deformed three-dimensionally, and wherein the impedance adjusting means is arranged in parallel to each transducer or to a predetermined set of transducers. In the ultrasonic irradiation apparatus according to the present invention, the ultrasonic irradiation apparatus comprises the aforementioned impedance adjusting means, and thus it is possible to adjust the output allocation of each transducer so that the irradiation distribution of the ultrasonic waves within the object becomes a specified or even distribution.

In the ultrasonic irradiation apparatus according to the present invention, the ultrasonic irradiator may have an approximately resonant inductance to each ultrasonic transducer, which is adjustable, so that a sonic field from each ultrasonic transducer acquires a predetermined intensity ratio, and the inductance may be arranged in series to each ultrasonic transducer, or to a set composed of a predetermined number of ultrasonic transducers. In the ultrasonic irradiation apparatus according to the present invention, the ultrasonic irradiation apparatus comprises the adjustable inductance. Hence, it is possible to adjust the output allocation to each transducer so that the intensity distribution of the ultrasonic waves within the object becomes a specified or even distribution.

The ultrasonic irradiation apparatus according to the present invention is characterized in that the ultrasonic irradiator, having a plurality of ultrasonic transducers arranged in plane on a surface of a rigid sheet member, is arranged inside of a planar bag which contains a fluidic material as an ultrasonic conducting medium, and which has at least one flexible plane surface. Thus, the ultrasonic irradiation apparatus is capable of contacting an object having three-dimensionally curved surfaces, such as a living body, with the flexible plane surface of the planar bag. Therefore, even though a plurality of ultrasonic transducers are installed on the surface of the rigid sheet member in the ultrasonic irradiator arranged inside the planar bag, it is possible to easily irradiate with ultrasonic waves a wide area of an object having three-dimensionally curved surfaces.

BRIEF DESCRIPTION OF THE DRAWINGS

FIG. 6 is a plan figure showing a third example of the ultrasonic irradiation apparatus according to the second embodiment of the present invention.

FIG. 7 is a plan figure showing a fourth example of the ultrasonic irradiation apparatus according to the second embodiment of the present invention.

PREFERRED EMBODIMENTS OF THE PRESENT INVENTION

Embodiments of the present invention are described in detail by referring to the attached figures as follows.

Figure 1:
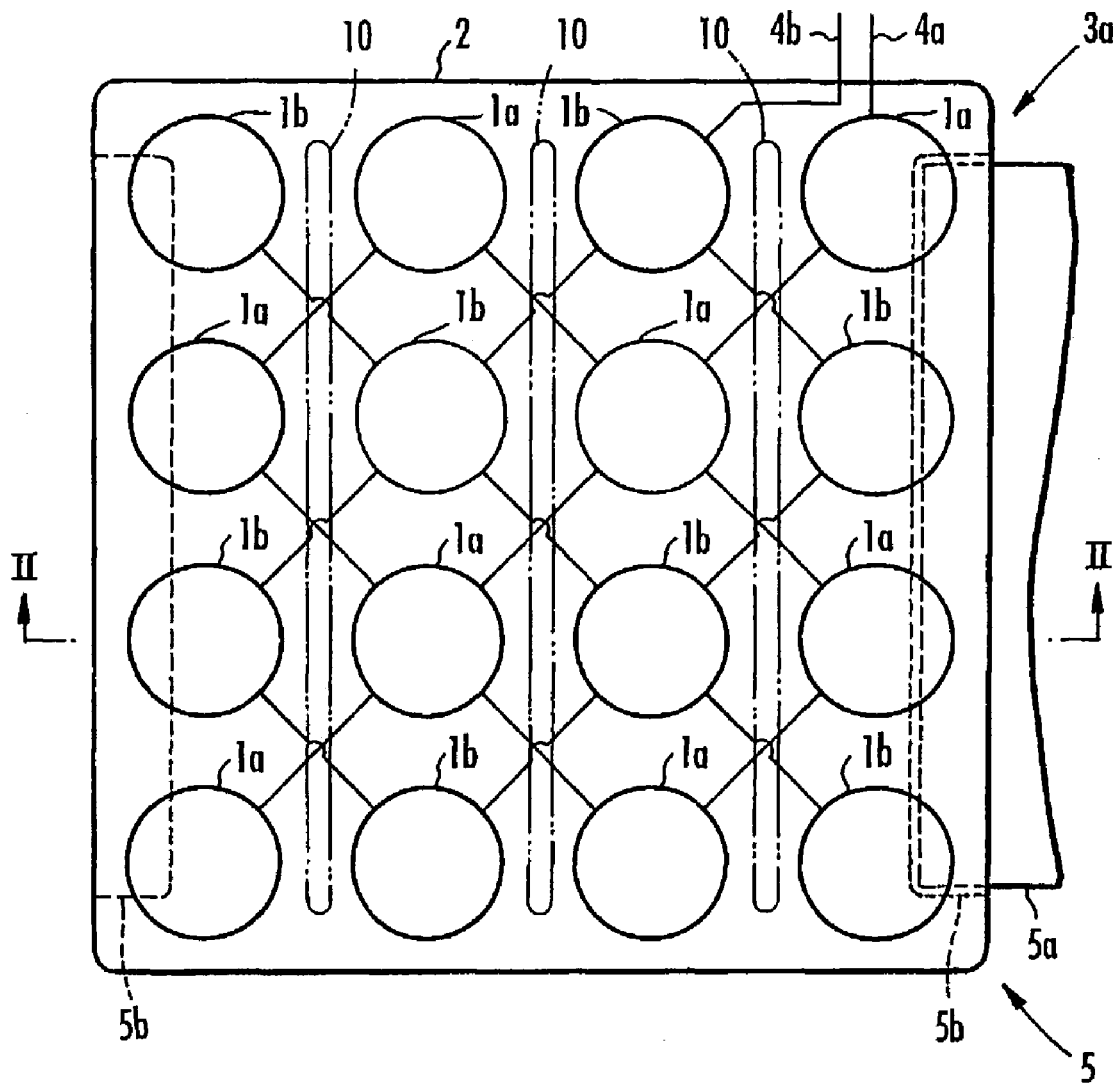
FIG. 1 is a plan figure showing an example of an ultrasonic irradiation apparatus according to a first embodiment of the present invention.
Figure 2:
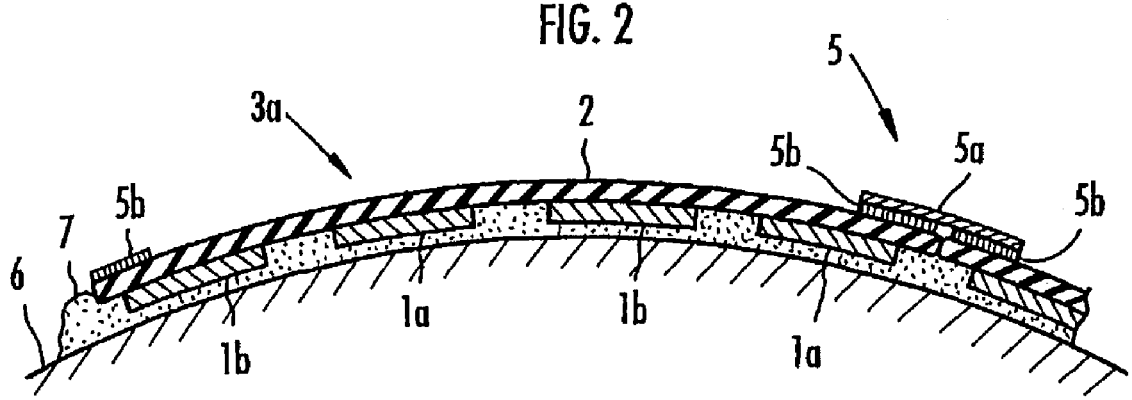
FIG. 2 is a cross sectional figure showing an example of usage, at the corresponding cross section II-II depicted in FIG. 1, of the ultrasonic irradiation apparatus according to the first embodiment.
Figure 3:
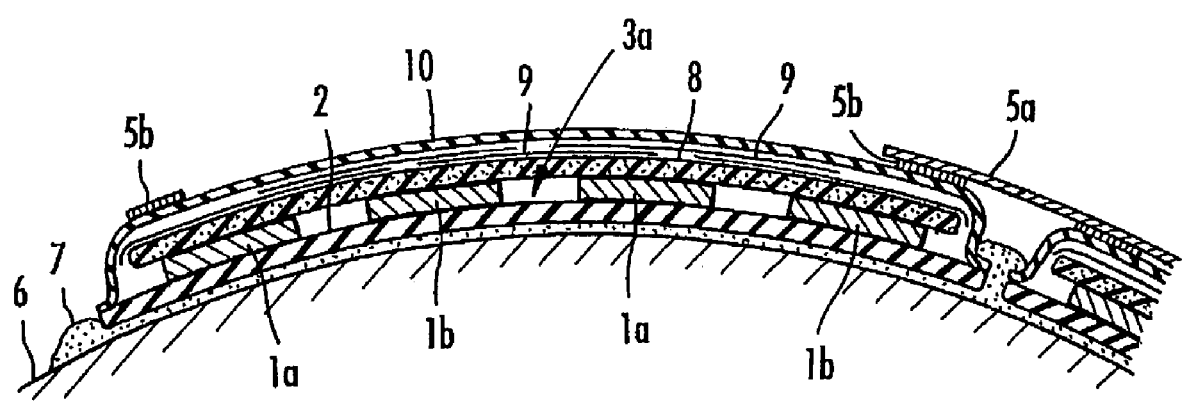
FIG. 3 is a cross sectional figure showing another example of usage, at the corresponding cross section II-II depicted in FIG. 1, of the ultrasonic irradiation apparatus according to the first embodiment.

First, with reference to FIG. 1 through FIG. 3, an ultrasonic irradiation apparatus according to the first embodiment of the present invention shall be described.

The ultrasonic irradiation apparatus, according to this embodiment is an apparatus for irradiating a living body with ultrasonic waves, mainly for lipolysis, but it can be also used for other purposes such as acceleration of the bloodstream, infiltration of an endermic medicine, and so on. In the first embodiment, as shown in FIG. 1, an ultrasonic irradiator 3a comprises a plurality of ultrasonic transducers 1a and 1b installed on one surface of a sheet member 2. In the case where the sheet member 2 is sound-conductive, the ultrasonic transducers 1a and 1b can be appropriately arranged on any of inside and/or outside planes of the sheet member 2.

The ultrasonic transducers 1a and 1b may be ones having a driving electrode arranged on one plane of a piezoelectric element composed of ceramics (e.g., PZT (Pb(Zr*Ti$_3$)O$_3$), etc.) and an opposed ground electrode arranged on the other plane of the piezoelectric element. The ultrasonic transducers 1a and 1b output ultrasonic waves by applying a drive voltage of a predetermined frequency between the driving electrode and the opposed ground electrode. The ultrasonic transducers 1a and 1b can be a composed one of mutually adhered two piezoelectric elements in a pair, by placing each driving electrode in contact between opposed ground electrodes at both outer sides. In this embodiment, each group of ultrasonic transducers 1a and 1b is connected via conductors 4a and 4b to respective different drive systems, and for example, can be turned on or off at a mutually inverse timing. Of course, the device can be driven by keeping all of them in a same condition, without being separated into respectively different groups such as 1a or 1b.

The sheet member 2 is preferably made of a material that is flexible and/or elastic, and which can be formed by several types of rubber sheet members, foamed rubber sheet members such as expanded butylene or expanded silicon, fabrics or unwoven textiles, etc. Because the sheet member 2 has flexibility and elasticity, each position of the ultrasonic transducers 1a and 1b can be adaptively changed to fit to a three-dimensionally curved living body surface, such as the abdominal region, the thigh, the buttocks, the chin and so on. The ultrasonic transducers 1a and 1b are normally installed on the sheet member while being set slightly apart by a thickness of the transducer, so that the opposed ground electrode side can contact the living body surface.

The ultrasonic irradiator 3a further comprises a joining member 5 composed of a pair of plane fasteners 5a and 5b (e.g., Magic Tape manufactured by KURARAY CO., LTD. [Trademark]) at the periphery of the ultrasonic irradiator 3a, and a plurality of ultrasonic irradiators 3a are arranged to be joined together via the joining member 5.

In the ultrasonic irradiator 3a, it is preferable to arrange an air back layer, such as a material containing air foam or an air layer, on the back side of the assembly made up of the sheet member 2 and the ultrasonic transducers 1a and 1b, so as to reflect, by means of the air foam or air layer, the radiation of ultrasonic waves coming from the ultrasonic transducers 1a and 1b toward the living body side contact sheet member 2. Thereby, all of the ultrasonic energy is output from each of the ultrasonic transducers 1a and 1b toward the front living body contact side of the sheet member 2 assembly and an output plane is formed at the front side. In this case, the resonance frequency characteristic of the ultrasonic transducers 1a and 1b acquires a sharp narrow band. However, a narrow band is sufficient in the case where the ultrasonic transducers 1a and 1b irradiate continuous waves (CW).

However, in the case where the ultrasonic transducers 1a and 1b irradiate pulse waves, it is necessary for the spectrum to be of a broad band, by arranging a sonic absorbing layer (e.g., a rubber containing a metal powder, etc.) on the back side of the sheet member 2 and/or the ultrasonic transducers 1a and 1b. The air back layer or the sonic absorber layer may be laminated onto the back side of the assembly made up of the sheet member 2 and the ultrasonic transducers 1a and 1b. Alternatively, the sheet member 2 may be arranged so as to function as the air back layer by including air foams therein, or to function as the sonic absorber layer by including metallic powders therein. The front side of ultrasonic irradiator 3a can have an impedance layer acoustically matched with the living body, an insulation layer and a ground electrode layer, etc., formed in the irradiator on the side of the living body.

It is preferable that an insulation layer and/or a conductive layer be further arranged on the front side of the assembly made up of the sheet member 2 and the ultrasonic transducers 1a and 1b, by laminating such layers on the electrode or by lapping them at a certain distance. Thereby, it is possible to avoid an electric current from leaking to the living body, or for unnecessary electromagnetic radiation to be radiated outwards, because the conductive layer can be connected to a ground electric potential. The conductive layer may be arranged by using a process for adding conductivity to the back surface of the sheet member 2, or by laminating an aluminum fiber fabric onto the back side of the sheet member 2 assembly.

In the case where the sheet member 2 is composed of several types of hard rubber sheet material, the sheet member 2 may possess only flexibility without elasticity. In this case, it is preferable to arrange a plurality of linear recesses 2a (as indicated by hypothetical lines) on the surface of the sheet member 2, as depicted in FIG. 1. By providing the linear recesses 2a in the sheet member 2, when the sheet member 2 is deformed along the linear recesses 2a, the opening of the linear recesses 2a is changed into a ship shape by causing the upper edges of the linear recesses 2a to move apart, and the sheet member 2 also becomes easily deformable in a direction transverse to the linear recesses 2a.

The linear recesses 2a are arranged between the ultrasonic transducers 1a and 1b and need not necessary be straight lines. Further, it is not necessary that the linear recesses 2a be mutually parallel. Further, the width of the linear recesses 2a may be freely determined. The linear recesses 2a are arranged from one surface toward the other surface in the sheet member, and may or may not penetrate through to the other surface.

Next, it shall be explained, by referring to FIG. 1 and FIG. 2, how to use the ultrasonic irradiation apparatus according to the above embodiment.

In one exemplary usage, the ultrasonic irradiator 3a is shown cross sectionally in FIG. 2 corresponding to a portion of the cross section II-II shown in FIG. 1, wherein the ultrasonic transducers 1a and 1b are arranged to fit along a three-dimensionally curved surface of a living body 6 such as the abdominal region, the thigh, the buttocks, the chin, and so on. Then, the ultrasonic irradiator 3a is joined to an adjacent ultrasonic irradiator 3a with a joining member 5 composed of a pair of plane fasteners 5a and 5b, and a fluidic material layer 7, serving as an ultrasonic conducting medium, is provided between the living body 6 and the ultrasonic irradiator 3a.

The fluidic material layer 7 functions as an acoustic coupling medium for eliminating air between the ultrasonic transducers 1a and 1b and the living body 6, as well as for securing an acoustic coupling between the ultrasonic transducers 1a and 1b and the living body 6. A material for the fluidic material layer 7 is, e.g., acoustic jelly.

In the case where the ultrasonic irradiation apparatus irradiates a human with ultrasonic waves, it is required to wash and disinfect the ultrasonic irradiator 3a every time it is used, and so on. Therefore, when jelly is used as the fluidic material layer 7, the jelly is preferably water-soluble. The sheet member 2 is preferably waterproof and tolerant to disinfectants.

In the present ultrasonic irradiation apparatus, it is possible to interpose a soft material layer, such as a gel material like agar, in place of the fluidic material layer 7, and further to interpose similar or other materials along with the sound conducting sheet member 2. For example, a hygroscopic polymer, containing a large amount of water, etc., is applicable as the gel material like agar, and a non-foam containing rubber or the like is applicable as the sound conductive sheet member 2.

Further, the fluidic material layer 7, or the material substituted therefor, preferably is formed of a heatable or refrigeratable high specific heat material (hot pack or cold pack), whereby it is possible to enhance the effectiveness of the irradiation with ultrasonic waves to the living body 6 by controlling the temperature of the fluidic material layer 7, or the substituted material, by heating or cooling thereof in advance. In the case of irradiating a human with ultrasonic waves, the tactile feeling of the object can be improved by using the fluidic material layer 7, or the substituted material, which has been heated or cooled.

In the ultrasonic irradiation apparatus, fats in the living body 6 are decomposed (lipolysis) by irradiation with ultrasonic waves (e.g. 500 kHz at 110 mW/cm$^2$). Then, when sonic fields of ultrasonic waves from the ultrasonic transducers overlap within the living body 6, due to mutual interference, some parts having added pressure amplitudes and other parts having reduced pressure amplitudes are generated. Thus, in such overlapping portions of the pressure amplitude, the irradiation dose of ultrasonic waves may be excessive or insufficient.

When the irradiation dose of ultrasonic waves becomes excessive at certain portions in the living body, heat may be generated or tissues may become injured in such portions. Therefore, the Thermal Index (TIS) and the Mechanical Index (MI) have been introduced as a measure of the irradiation dose of ultrasonic waves to the living body by Food and Drug Administration (FDA) of the United States of America (U.S.A.). According to FDA publications, a safe range for irradiation values to the living body is TIS=2 and MI=0.3.

TIS is a numerical value for soft tissues in the Thermal Index, wherein TIS=2 means that the temperature of the soft tissues is raised 2° C. during continuous irradiation of ultrasonic waves. For a living body at 36° C., this implies a temperature of 38° C. This temperature is often encountered in catching a cold and is positively safe to the living body.

On the other hand, the Mechanical Index indicates a degree where tissues are injured by cavitation. MI=0.3 is a safe level to any mammal.

When the ultrasonic irradiation apparatus irradiates with ultrasonic waves of 500 kHz at 110 mW/cm$^2$, as mentioned above for lipolysis in the living body 6, even if the strength of ultrasonic waves becomes 800 mW/cm$^2$ due to overlapping of the ultrasonic waves, it is still within a safe range because TIS remains 2 or below and MI remains 0.3 or below. Normally, upon overlapping of two ultrasonic transducers, the ultrasonic wave strength never exceeds being doubled, i.e., 220 mW/cm$^2$ or more. But, during other uses, the overlapping of the ultrasonic transducers 1a and 1b should not be ignored.

Therefore, in the ultrasonic irradiation apparatus, the ultrasonic transducers 1a and 1b are each driven respectively by different drive systems, which are arranged in a cross-stripes pattern. Thereby, each of ultrasonic transducers 1a and 1b is arranged to avoid unnecessary overlapping of the sonic fields of the ultrasonic transducers 1a and 1b, so that each ultrasonic transducer 1b is in the center of each rhombus making up a system (or group) of the ultrasonic transducers 1a. Further, each of the ultrasonic transducers 1a is in the center of each rhombus making up a system (or group) of the ultrasonic transducers 1b.

In the ultrasonic irradiation apparatus, it is possible to drive each of the ultrasonic transducers 1a and 1b via each of conductors 4a and 4b which are respectively connected to different driving systems, by turning them ON/OFF at a mutually inverse timing. Thereby, overlapping of the sonic fields in the ultrasonic transducers 1a and 1b is never generated.

To avoid that the irradiation dose of ultrasonic waves becomes excessive or insufficient due to overlapping of the sonic fields of the ultrasonic transducers 1a and 1b, an example of driving the ultrasonic transducers 1a and 1b by turning them ON/OFF at a mutually inverse timing has been discussed. However, as an alternative, while constantly driving one of the ultrasonic transducers 1a or 1b at a fixed timing, the other one can be driven via a phase-shifted circuit, which is continuously changed in phase, or can be driven by continuously and slightly changing its frequency. Thereby, the added and reduced portions of the pressure amplitudes due to interference are continuously kept moving in the living body 6, so that the irradiation dose of ultrasonic waves is averaged within the region irradiated by the ultrasonic waves. Therefore, it is possible to keep the irradiation dose of ultrasonic waves from becoming either excessive or insufficient. It is also possible to make the distribution of the output strength (mW/cm$^2$) uniform at the irradiation output plane, or to make the distribution shape like a plateau or mountain, by weakening the edge portion of the distribution and strengthening the center portion of the distribution.

Adjusting the output allocation for each of the ultrasonic transducers 1a and 1b may also be used in place of the method of changing the driving means of the ultrasonic transducers 1a and 1b.

As one method for adjusting the output allocation of each of the ultrasonic transducers 1a and 1b, it is applicable to connect a transformer for impedance conversion in parallel to the unit where each of the ultrasonic transducers 1a and 1b, or a plurality of ultrasonic transducers 1a and 1b, are connected in series or in parallel. Thereby, the ultrasonic transducer unit is connected to the secondary side of the transformer and a driving power source is connected to the primary side of the transformer. In the case of using a transformer for impedance conversion, it is possible to set the output allocation for each of the ultrasonic transducers or the unit at any ratio, by changing a turn ratio or coupling coefficient of the transformer (e.g., by changing the insertion degree of a magnetic core).

By connecting an inductance in series to each of the ultrasonic transducers, which is approximately resonant to each of the ultrasonic transducers 1a and 1b, or by connecting an inductance in series, which is approximate resonant to a unit made up from a plurality of ultrasonic transducers connected in series or parallel, it is also possible to adjust the output allocation of each ultrasonic transducer or that of the unit. It is also possible to achieve an effect of reducing an invalid electric power by arranging the inductance. The inductance is smaller in size than that of the transformer for impedance conversion, and can be installed for each of the ultrasonic transducers 1a and 1b or for the unit overall.

The arrangement of ultrasonic transducers 1a and 1b is not limited to the cross-stripes pattern arrangement depicted in FIG. 1, and may be any other arrangement, e.g., a hexagonal close-packed structure or the like. Also, the shape of each of the ultrasonic transducers 1a and 1b is not limited to a round shape, as depicted in FIG. 1 and can be freely designed in, e.g., square, rectangular or other patterns.

Next, referring to FIG. 3, another method for using the ultrasonic irradiation apparatus according to this embodiment shall be explained.

In the method described in FIG. 3, the ultrasonic irradiator 3a is arranged so as to make contact with the living body 6 via the fluidic material layer 7 under the surface of a side of the sheet member 2 opposite to the ultrasonic transducers 1a and 1b. In this case, ultrasonic waves from the ultrasonic transducers 1a and 1b are output through the sheet member 2 and transferred to the living body 6 through the fluidic material layer 7. Therefore, the sheet member 2 should be sound-conductive, and be composed of a material that does not contain substances which would reflect, and/or absorb ultrasonic waves, such as foam, gas or metal powder. For example, the material can be selected from among several types of rubber sheets such as, e.g., natural rubber, synthetic rubber or silicon rubber, etc. Materials containing substances which reflect and/or absorb ultrasonic waves, such as foamed rubber, foamed plastic, fabrics or textiles, etc., are not applicable in this situation.

It is preferable to arrange an air back layer 8 and an electromagnetic shielding layer 9 on the opposite upper surface of the ultrasonic transducers 1a and 1b on the sheet member 2, and to arrange a protective layer 10 covering the ultrasonic transducers 1a and 1b, the air back layer 8 and the electromagnetic shielding layer 9. The protective layer 10 is bonded to the sheet member 2 at a peripheral portion thereof and forms a bag-like construction. Further, the protective layer 10 contains the ultrasonic transducers 1a and 1b, the air back layer 8 and the electromagnetic shielding layer 9 in the back area between the sheet member 2 and itself. In this case, a joining member 5 (a pair of plane fasteners 5a and 5b) for joining the ultrasonic irradiator 3a is arranged at the peripheral portion of the protective layer 10.

The air back layer 8 can be made of a flexible sheet member composed of a foamed material such as foamed polyethylene or foamed rubber, etc. Further, the electromagnetic shielding layer 9 can be a flexible sheet member composed of a metal foil, a metal mesh or a conductive rubber, etc. In the ultrasonic irradiation apparatus depicted in FIG. 3, a plurality of electromagnetic shielding layers 9 are arranged overlapping each other so that each of them can freely slide.

As the protective layer 10, several types of rubber sheet members, foamed rubber sheet members, such as expanded butylene or expanded silicon, fabrics or unwoven textiles, etc., may be applicable. The protective layer 10 is preferably waterproof for improving disinfection. It is not necessary to fill any special material on the inside of the protective layer 10, and only air is sufficient. The air back layer 8 may also simply be an air layer, wherein air existing on the inside of the protective layer 10 may be used in place of the air back layer 8.

In the ultrasonic irradiation apparatus depicted in FIG. 3, because the ultrasonic irradiator 3a contacts with the living body 6 via a surface of the sheet member opposite to the ultrasonic transducers 1a and 1b, the ultrasonic irradiator 3a can smoothly slide along the three-dimensionally curved surfaces of the living body 6, and in the case of irradiating a human with ultrasonic waves, the contact feeling of the object can be improved. Because the ultrasonic transducers 1a and 1b are arranged on the sheet member 2, on a side opposite to the living body 6, the sheet member is also effective for protecting the ultrasonic transducers 1a and 1b.

Next, an ultrasonic irradiation apparatus according to a second embodiment of the present invention shall be explained with reference to FIG. 4 through FIG. 7.

Figure 4:
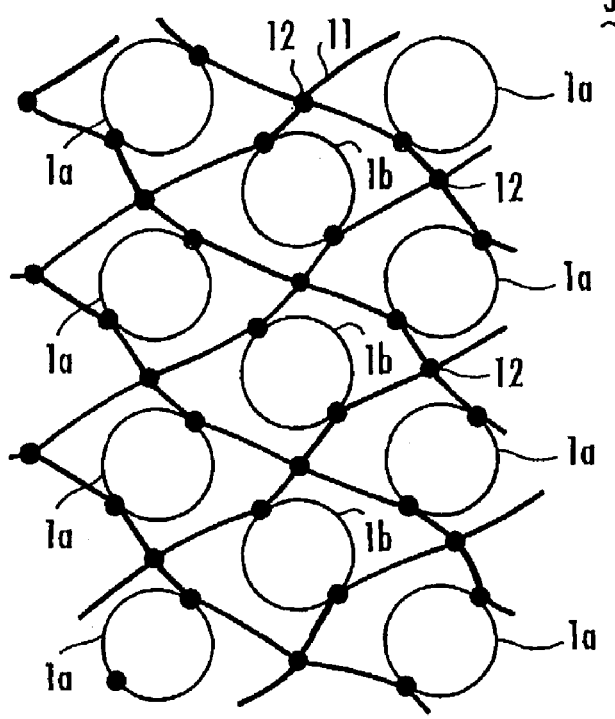
FIG. 4 is a plan figure showing a first example of an ultrasonic irradiation apparatus according to a second embodiment of the present invention.

In the ultrasonic irradiation apparatus, an ultrasonic irradiator 3b is composed of a plurality of ultrasonic transducers 1a and 1b installed on a net member 11 and arranged in a plane, as described in FIG. 4. The net member 11 is preferably composed of a material having flexibility and elasticity, wherein the net member 11 is formed of at least one type of material such as a string, a band, a spring, a chain and linked rods that are freely rotatable, and being fastened by knots 12. The ultrasonic transducers 1a and 1b are arranged in a checkered pattern within the net member 11 and are adhered to the net member 11. However, the arrangement of the ultrasonic transducers 1a and 1b is not limited to such a checkered pattern.

Figure 5:
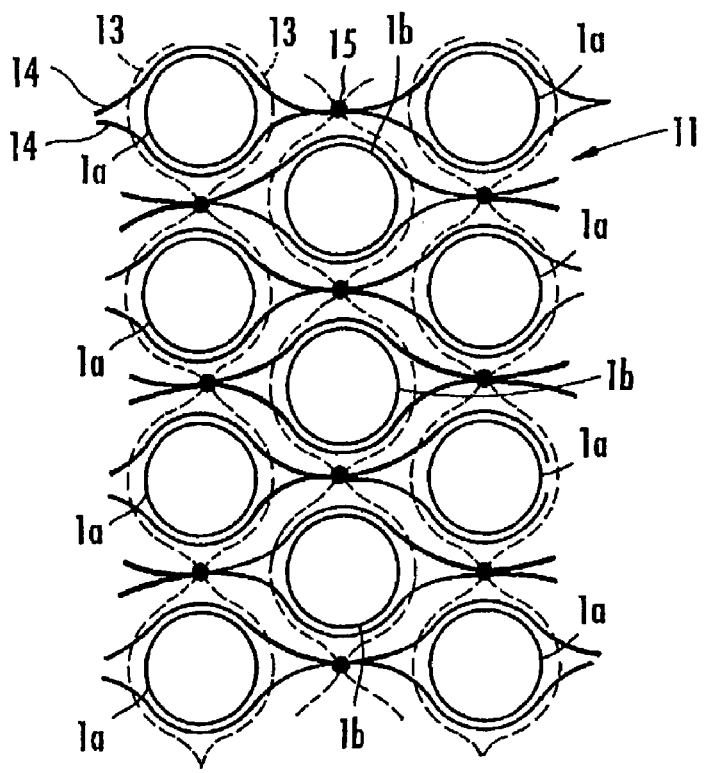
FIG. 5 is a plan figure showing a second example of the ultrasonic irradiation apparatus according to the second embodiment of the present invention.

The strings for forming the net member 11 may be, for example, a synthetic resin string, a rubber line (a rubber string) or a plastic filament, etc. In the event a band is used, the band for forming the net member 11 may be composed of, for example, plastic, rubber, textile, fabric, very thin metal foil, a spring or a chain, etc. The net member 11 may be composed of two longitudinal strings 13 and two lateral strings 14, as depicted in FIG. 5. The longitudinal string 13 and the lateral string 14 may be mutually knotted or bonded at an intersection 15. In this case, the ultrasonic transducers 1a and 1b may be adhered at their sides to the longitudinal string 13 and the lateral string 14, or it may be applicable to form a surrounding groove along a side plane of the transducer (although not indicated in the figure), and to arrange the ultrasonic transducers 1a and 1b so as to be constrained by binding the longitudinal string 13 and the lateral string 14 to such a groove.

In FIG. 5, the longitudinal string 13 is shown by a dotted line and the lateral string 14 is shown by a solid line, in order to make the relationship between the longitudinal string 13 and the lateral string 14 clear. Also, the longitudinal string 13 and the lateral string 14 are depicted in the figure as shown apart from the ultrasonic transducers 1a and 1b, to better show the existence of the longitudinal strings 13 and the lateral strings 14.

Further, in the ultrasonic irradiator 3b, as shown in FIG. 6, the ultrasonic transducers 1a and 1b may be installed on a plurality of bands 16. The plurality of bands 16 are mutually connected by, e.g., a string (not shown), so that the ultrasonic transducers 1a and 1b are arranged in a hexagonal close-packed structure to thereby form the net member 11.

In the ultrasonic irradiator 3b as shown in FIG. 7, each of the ultrasonic transducers 1a and 1b may be connected by two strings 17, wherein the two strings 17 are mutually connected by, e.g., another string (not shown), so that the ultrasonic transducers 1a and 1b are arranged in a hexagonal close-packed structure to thereby form the net member 11. The arrangement of the ultrasonic transducers 1a and 1b is not limited to a hexagonal close-packed structure.

In this case, the ultrasonic transducers 1a and 1b have a surrounding groove 18 on the side and are constrained by the strings 17, which are appropriately positioned. The two strings 17 are banded together by center holes of spacers 19, which are arranged between the ultrasonic transducers 1a and 1a, or ultrasonic transducers 1b and 1b.

In the ultrasonic irradiator 3b shown in FIG. 7, it may be applicable to use, e.g., thin bands or thin springs in place of the strings 17.

The ultrasonic irradiators 3b shown in FIG. 4 through FIG. 7 may have the same structure as the ultrasonic irradiator 3a, except that the ultrasonic transducers 1a and 1b are installed on the net member 11.

Figure 8:
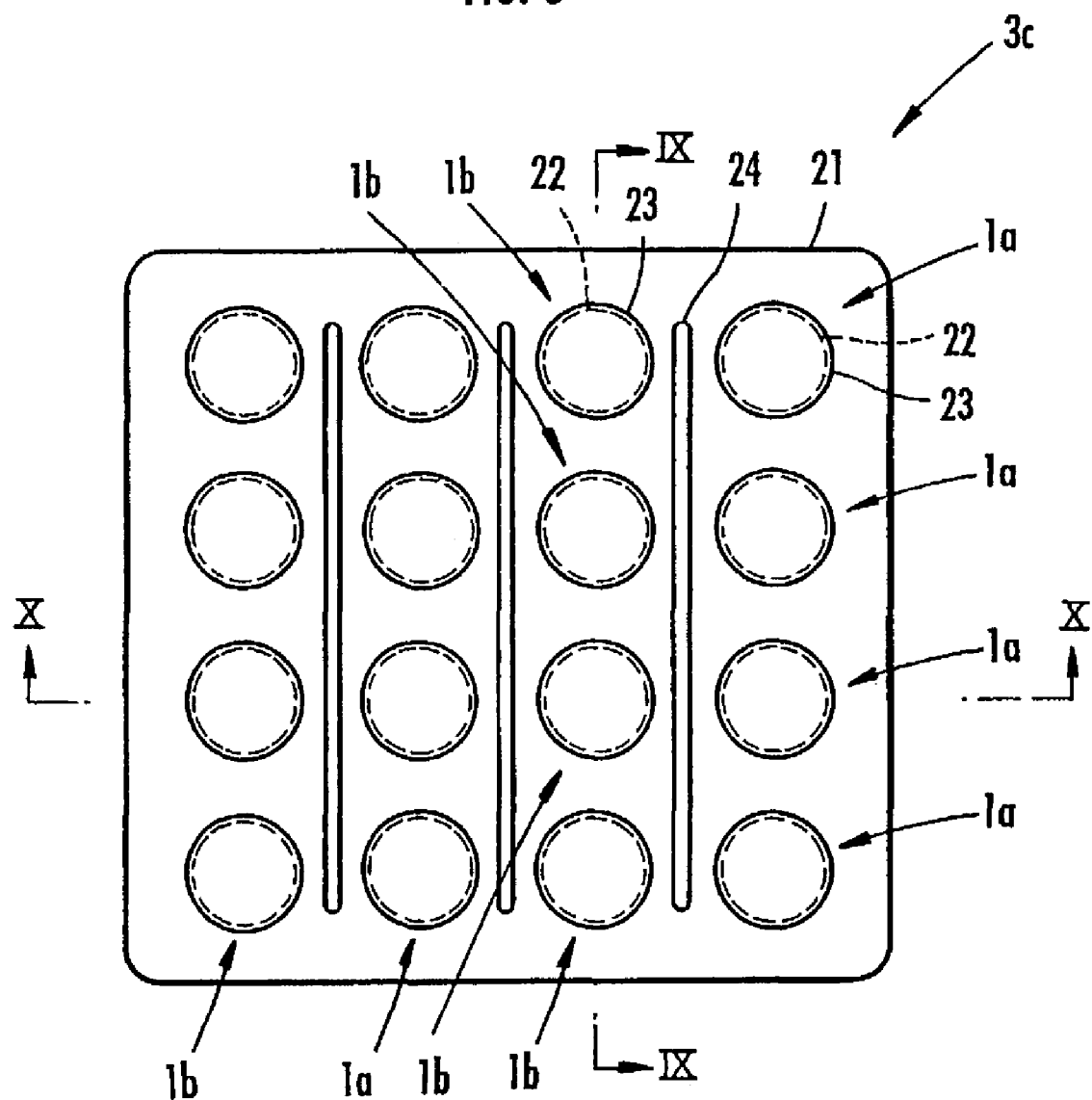
FIG. 8 is a plan figure showing an example of an ultrasonic irradiation apparatus according to a third embodiment of the present invention.
Figure 9:
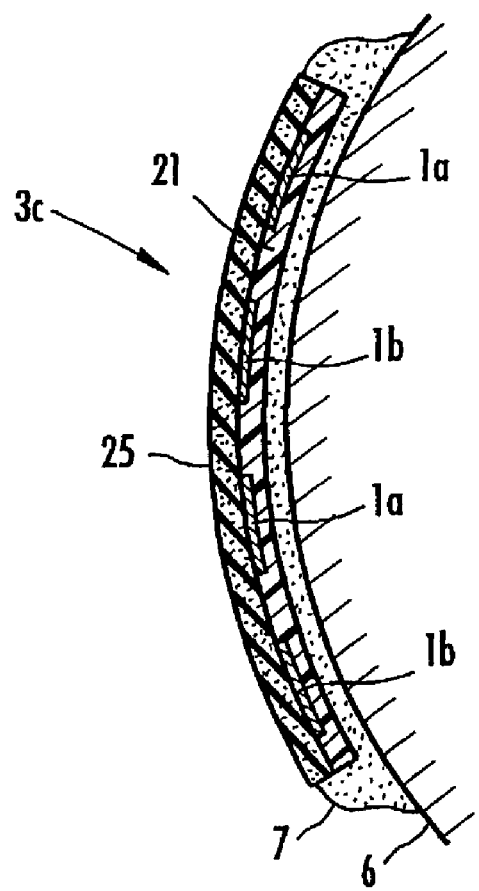
FIG. 9 is a cross sectional figure showing the usage at the cross section IX-IX depicted in FIG. 8, of the ultrasonic irradiation apparatus according to the third embodiment.
Figure 10:
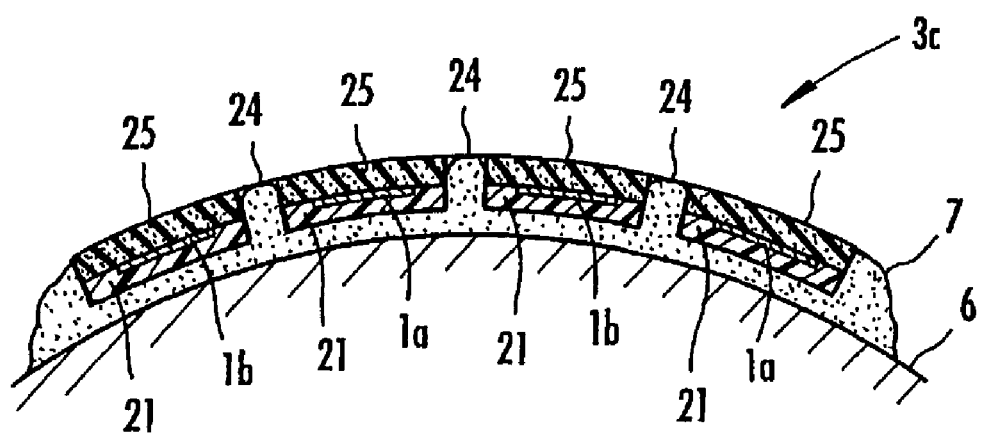
FIG. 10 is a cross sectional figure showing the usage at the cross section X-X depicted in FIG. 8, of the ultrasonic irradiation apparatus according to the third embodiment.

Next, referring to FIG. 8 through FIG. 10, an ultrasonic irradiation apparatus according to a third embodiment of the present invention shall be explained.

In the ultrasonic irradiation apparatus of this embodiment, a plurality of ultrasonic transducers 1a and 1b, composed of a driving electrode 22 formed on one plane of a flexible piezoelectric sheet member 21 and an opposed ground electrode 23 formed on the other plane of the flexible piezoelectric sheet member 21, are arranged in a plane facing each other, for forming the ultrasonic irradiator 3c as depicted in FIG. 8. In the ultrasonic irradiator 3c, the ultrasonic transducers 1a and the ultrasonic transducers 1b are alternately arranged in each row of a tessellate arrangement (cross-stripes pattern).

As the flexible piezoelectric member 21, a sheet of an organic piezoelectric material, like PVDF, or a sheet formed under an electric field from a plastic containing fine-grained piezoelectric ceramic, such as PZT, may be used. The driving electrode 22 and the opposed ground electrode 23 may be formed by a metal vapor deposition method on a surface of the flexible piezoelectric member 21.

The flexible piezoelectric member 21, when composed of the materials mentioned above, generally has flexibility, but is not sufficient in elasticity. Therefore, the flexible piezoelectric member 21 preferably has a plurality of linear recesses 24 on its surface. In the ultrasonic irradiator 3c depicted in FIG. 8, the linear recesses 24 are arranged in a straight pattern between the ultrasonic transducers 1a and 1b, and the plurality of linear recesses 24 are formed to be mutually parallel. Further, the linear recesses 24 are formed from one surface of the flexible piezoelectric member 21 toward the other surface, so as to penetrate the flexible piezoelectric member 21 in a thickness direction thereof.

Because the flexible piezoelectric member 21 includes linear recesses 24 in the ultrasonic irradiator 3c, when deformed along the linear recesses 24, the opening portions of the linear recesses 24 can be deformed into a ship shape, as a result of the upper edges of the linear recesses 24 moving apart, and it can also be easily deformed in a direction transverse to the linear recesses 24. Thereby, the positions of the ultrasonic transducers 1a and 1b, provided in the ultrasonic irradiator 3c, are mutually and flexibly deformable three-dimensionally.

The linear recesses 24 can be arranged between the ultrasonic transducers 1a and 1b, but are not limited to being in a linear shape, and need not necessarily be mutually in parallel. Moreover, they may be freely arranged, for example, the ultrasonic transducers 1a and 1b can be arranged in a hexagonal close-packed structure, wherein the shape of the linear recesses 24 can be a curved waveform line winding between the ultrasonic transducers 1a and 1b. Further, the linear recesses 24 should be formed from one surface of the flexible piezoelectric member 21 toward the other surface, and can be non-penetrating with respect to the flexible piezoelectric member 21. In the case that they do not penetrate the flexible piezoelectric member 21, the linear recesses 24 may be arranged alternately on one surface and the other surface of the flexible piezoelectric member 21.

Further, when the linear recesses 24 in FIG. 8 are formed by penetrating the flexible piezoelectric member 21 from one surface to the other surface, a portion of the linear recesses 24 should not reach to a peripheral edge, so as not to divide the flexible piezoelectric member 21 into pieces. However, in the case where the linear recesses 24 do not penetrate through the thickness of the flexible piezoelectric member 21, the linear recesses 24 may be arranged over the flexible piezoelectric member 21 from one peripheral edge to the opposed peripheral edge.

The ultrasonic irradiator 3c shown in FIG. 8 can have the same structure as the ultrasonic irradiator 3a, except that the ultrasonic transducers 1a and 1b are formed from the flexible piezoelectric member 21.

Next, referring to FIG. 9 and FIG. 10, a method for using the ultrasonic irradiation apparatus shall be explained.

The ultrasonic irradiator 3c shown in FIG. 9 corresponds to the cross section IX-IX of FIG. 8, whereas the ultrasonic irradiator 3c shown in FIG. 10 corresponds to the cross section X-X of FIG. 8. The ultrasonic transducers 1a and 1b are actually composed of the driving electrode 22 and the opposed electrode 23, and are arranged facing each other actually on both planes of the flexible piezoelectric member 21, as depicted in FIG. 8. However, for convenience of illustration, they are shown in FIG. 9 and FIG. 10 as if the ultrasonic transducers were arranged on one plane only of the flexible piezoelectric member 21, similar to the arrangement of FIG. 1.

In the ultrasonic irradiation apparatus of the present embodiment, the ultrasonic irradiator 3c is deformable in a direction along the linear recesses 24 as depicted in FIG. 9 as a result of the flexibility of the flexible piezoelectric member 24. The ultrasonic irradiator 3c is also deformable in a direction transverse to the linear recesses 24, as depicted in FIG. 10, because the opening portions of the linear recesses 24 can be changed into a ship shape by the upper edges of the linear recesses 24 moving apart.

Thereby, the ultrasonic irradiator 3c can be deformable three-dimensionally, as depicted in FIG. 9 and FIG. 10, and the ultrasonic transducers 1a and 1b are fitted along the three-dimensional curved surfaces of the living body 6 such as the abdominal region, the thigh, the buttocks, the chin and so on. Then, a fluidic material layer 7, namely an ultrasonic conducting medium, is to be placed between the living body 6 and the ultrasonic irradiator 3c.

The ultrasonic irradiator 3c irradiates with ultrasonic waves, in the manner indicated in FIG. 9 and FIG. 10, and thereby induces lipolysis within the living body 6 or performs other processes.

The ultrasonic irradiator 3c may have a reinforcement material layer 25 on the side opposed to the living body 6 in the flexible piezoelectric member 21. The reinforcement material layer 25 may be composed of a flexible electric shielding material, containing foams, or an air back layer for reflecting ultrasonic waves may also be used as the reinforcement material layer 25.

The reinforcement material layer 25 prevents leakage of electric current to the living body, or prevents unnecessary external electromagnetic radiation, when a conductive layer is further formed on a surface opposed to the flexible piezoelectric member 21 and the conductive layer is kept at a ground electric potential. The reinforcement material layer 25 may further include a protective layer, composed of flexible and elastic foamed rubber, on the outside thereof.

The ultrasonic irradiator 3c may further have a protective layer (not shown), which is a living body contact sheet, provided between the surface opposed to the reinforcement material layer of the flexible piezoelectric member and the surface of the living body 6. When the living body contact sheet is formed on the side of the living body 6, it is composed of a sound-conducting material, such as a rubber sheet which is flexible and/or elastic and does not contain foams therein, so that ultrasonic waves are able to pass therethrough. The protective layer preferably is attached with, e.g., epoxy adhesives, so as not to contain air between the flexible piezoelectric member 21 and itself, at least within areas where it is in contact with the ultrasonic transducers 1a and 1b. in order to transmit ultrasonic waves successfully.

In each of the ultrasonic irradiators 3a, 3b and 3c, the ultrasonic transducers 1a and 1b may be arranged in a cross-stripes or checkered pattern, as depicted in FIG. 1, FIG. 4 and FIG. 5, or may be arranged in a hexagonal close-packed structure, as depicted in FIG. 6 and FIG. 7. Further, in the tessellate (cross-stripes) arrangement, as depicted in FIG. 8, the ultrasonic transducers 1a and the ultrasonic transducers 1b may be alternately arranged in each row of the tessellate arrangement.

This is preferable because, while moving the ultrasonic irradiator along surfaces of the living body 6, a trajectory of the ultrasonic transducers 1a and a trajectory of the ultrasonic transducers 1b are overlapped irrespective of the driving direction, and thereby it is possible to eliminate a portion where the living body 6 is not irradiated with ultrasonic waves, based on arranging the ultrasonic transducers 1a and 1b in a hexagonal close-packed structure, as depicted in FIG. 6 and FIG. 7.

In each of the figures, the ultrasonic transducers 1a and 1b are shown as circles in plan view, but they are not limited to circles and may be of any shape. In the ultrasonic irradiator 3c depicted in FIG. 8, the ultrasonic transducers 1a and 1b can be easily formed in any shape, because the driving electrode 22 and the opposed electrode 23 forming the ultrasonic transducers 1a and 1b are formed on the surface of the flexible piezoelectric member 21 by means of a metal vapor deposition method.

Figure 11:
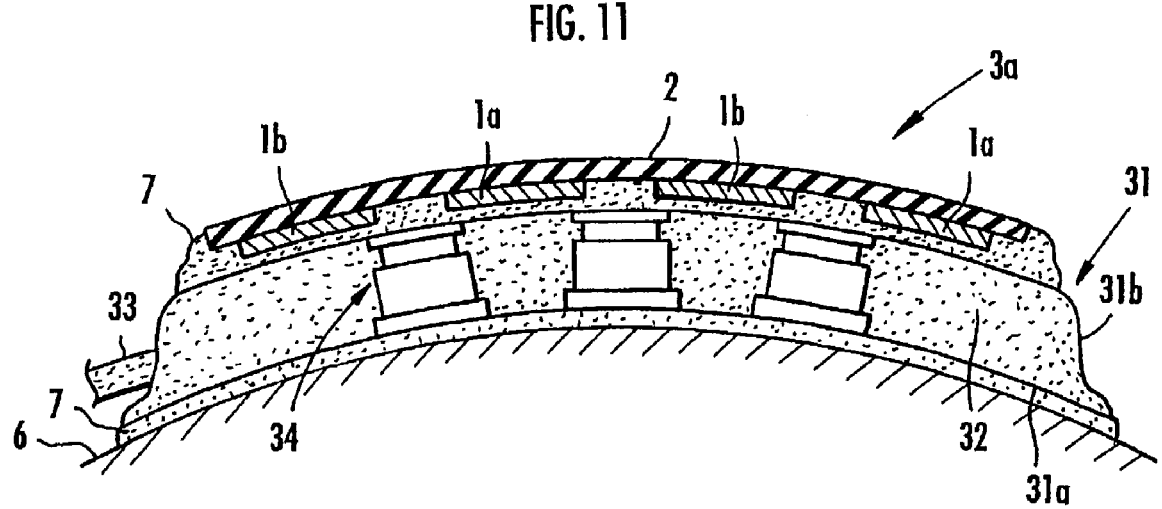
FIG. 11 is a cross sectional figure showing an example of an ultrasonic irradiation apparatus according to a fourth embodiment of the present invention.
Figure 12:
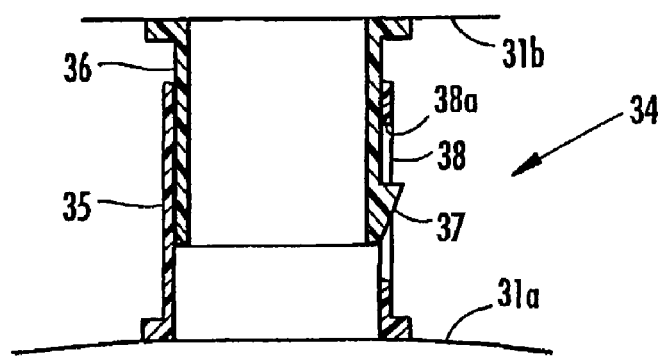
FIG. 12 is a cross sectional figure showing an enlarged primary portion of FIG. 11.
Figure 13:
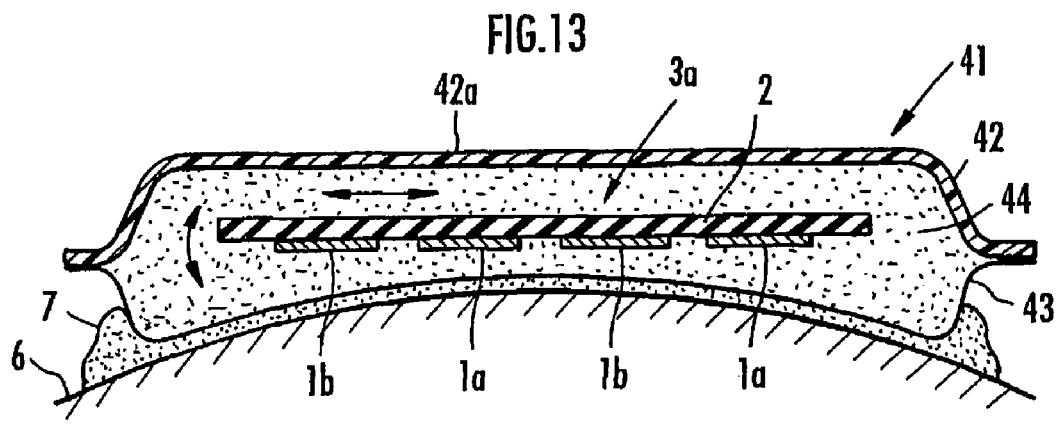
FIG. 13 is a cross sectional figure showing one example of an ultrasonic irradiation apparatus according to a fifth embodiment of the present invention.

Next, referring to FIG. 11 and FIG. 12, an ultrasonic irradiation apparatus according to the fourth embodiment of the present invention shall be explained.

In the ultrasonic irradiation apparatus, the ultrasonic irradiator 3a is installed on a surface of a flexible planar bag 31 containing a fluidic material layer 7, as depicted in FIG. 11. The planar sheet (bag) 31 is composed of a soft material having both flexibility and elasticity, and contains a fluidic material 32 as an ultrasonic conducting medium.

The ultrasonic irradiation apparatus is placed in contact with an object, such as a living body 6, via the fluidic material layer 7 on the surface of the planar bag 31, and irradiates the object with ultrasonic waves via the planar bag by the ultrasonic irradiator 3a.

Then, in the ultrasonic irradiation apparatus, it is possible to change the thickness of the planar bag 31 containing the fluidic material 32, as well as to change the relative position between the object and the ultrasonic transducers 1a and 1b installed in the ultrasonic irradiator 3a. Thereby, the overlapping positions of the irradiated ultrasonic waves within the object may be changed and an excess or insufficient irradiation dose of ultrasonic waves at a specific area of the object can be avoided.

Further, the planar bag 31 can be removed from the ultrasonic irradiator 3a and can be heated using a microwave oven or can be cooled using an electric refrigerator.

Because the planar bag 31 is flexible and contains the fluidic material 32, the thickness or shape of the planar bag 31 can be changed. However, it is preferable that the planar bag 31 has a tube 33 at a side plane thereof, for channeling the inside and outside, wherein the tube 33 is connected to a pump (not shown). Thereby, the pump can supply the fluidic material 32 to the planar bag 31 through the tube 33 or discharge the fluidic material 32 from the planar bag 31, and the thickness or shape of the planar bag 31 can be changed in a time sequence, by changing an amount of the fluidic material 32 contained in the planar bag 31. The meaning of "changed in a time sequence" includes changing at any time-range, or randomly, and is not limited to changing at a predetermined time period exactly.

In the planar bag 31, a partial deviation of the fluidic material 32 is caused inside the planar bag 31, namely, a partial amount of the fluidic material 32 within the planar bag 31 is excessively increased, being affected by supplying or discharging the fluidic material 32 by a pump or though the function of the gravity, etc., wherein the distance between the object and the ultrasonic transducers 1a and 1b installed in the ultrasonic irradiator 3a may be partially varied to become long or short. Further, when the ultrasonic irradiator 3a and the planar bag 31 are applied to a vertical surface of the living body 6, the fluidic material 32 is gathered at a lower portion. As a result, the lower portion is expanded, the upper portion is narrowed, the surface of ultrasonic irradiator 3a is greatly inclined, and it is difficult to contact curved surfaces of the living body 6. As the remedy, the planar bag 31 has a connection member 34, connecting an upper plane and a bottom plane within the planar bag 31, for keeping the thickness of the planar bag 31 within a predetermined range.

The connection member 34 is composed of a cylindrical member 35 installed on an inner wall 31a of the bottom plane in the planar bag 31 and a cylindrical member 36 installed on an inner wall 31b of the upper plane in the planar bag 31, wherein the cylindrical member 36 is inserted inside cylindrical member 35, so as to slide along an inner wall of the cylindrical member 35, as depicted in the enlarged view of FIG. 12. The cylindrical member 36 has a claw member 37 on a side plane thereof, and includes a wide slit (not shown) in an axial direction of the cylinder. The member 36 having the claw 37 is inserted into the cylindrical member 35 from the upper side by elastic deformation of the cylindrical member 36, and the claw 37 is restored and inserted in an opening 38 provided in a side wall of the cylinder 35. Then, the claw member becomes slidingly engaged with the cylinder 35. Sliding of the claw member 37 is limited at an upper end 38a of the opening 38, and thereby the thickness of the planar bag 31 is maintained within a predetermined range.

In the ultrasonic irradiation apparatus, the fluidic material 32 contained in the planar bag 31 may be a heatable or refrigeratable high specific heat material. In the case where the fluidic material 32 is a high specific heat material, the planar bag 31 may be detached and the fluidic material 32 in the detached planar bag 31 can be heated by, e.g., a microwave oven or cooled by, e.g., an electric refrigerator. It is possible to improve the effectiveness of ultrasonic irradiation to the object by irradiating the living body surface at a high temperature or a low temperature. Further, in the case where the object is a human, the tactile feeling of the person being irradiated can be improved by heating or cooling the fluidic material 32, as has been described above.

For example, a mixture of water, propylene glycol and methylcellulose may be applicable as the heatable fluidic material 32. For example, a mixture of water, hygroscopic polymer and polyhydric alcohol may be applicable as the refrigeratable fluidic material 32.

In the ultrasonic irradiation apparatus, the ultrasonic irradiator 3a is installed on the surface of the flexible planar bag 31 containing the fluidic material layer 7, and can be freely installed or detached, as depicted in FIG. 11. However, the ultrasonic irradiator 3a may also be integrated together with the surface of the planar bag 31 as a single unit. In this case, it should be arranged so that air can never exist between the planar bag 31 and the ultrasonic transducers 1a and 1b.

In the ultrasonic irradiation apparatus, the thickness of the planar bag 31 is kept within a predetermined range by the connection member 34 composed of the cylindrical members 35 and 36, as shown in FIG. 12. However, alternatively, it is possible to tie the upper plane and the bottom plane at the corresponding position within a predetermined distance in the planar bag 31 using, e.g., flexible strips or string members.

In the ultrasonic irradiation apparatus, any one of the ultrasonic irradiators 3b shown in FIG. 4 through FIG. 7, or the ultrasonic irradiator 3c shown in FIG. 8, may be used instead of the ultrasonic irradiator 3a.

Next, referring to FIG. 13 through FIG. 19, an ultrasonic irradiation apparatus according to a fifth embodiment of the present invention shall be explained.

In the ultrasonic irradiation apparatus, the ultrasonic irradiator 3a is arranged inside of a flexible planar bag 41. One plane of the flexible planar bag 41 is composed of a rigid member 42, and the other opposed plane is composed of a soft material 43 having flexibility and elasticity, which serves as an acoustic window. Further, the planar bag 41 contains a fluidic material 44 as an ultrasonic conductive medium. The ultrasonic irradiator 3a is arranged so as to be freely moved in parallel along a plane area 42a of the rigid material 42, or to be freely tilted in reference to the plane area 42a, as indicated by the arrows in FIG. 13.

In the ultrasonic irradiation apparatus, the planar bag 41 is in contact with the living body 6, via the fluidic material layer 7, at the output window composed of the soft material 43. Namely, at least one plane of the ultrasonic irradiator 3a (the plane of the soft material 43 in the present embodiment) irradiates an object with ultrasonic waves via the flexible planar bag 41. Because one plane of the planar bag 41 is composed of a rigid material 42, the bag is easily handled by holding the side of the rigid material 42.

Because the ultrasonic irradiator 3a is arranged so as to be freely moved along the plane area 42a of the rigid material 42, or to be freely tilted with respect to the plane area 42a, in the ultrasonic irradiation apparatus, the relative position between the object and the ultrasonic transducers 1a and 1b can be changed. Therefore, an overlapping portion of the ultrasonic waves from the ultrasonic transducers 1a and 1b with respect to the object is varied inside of the object, and an excessive or insufficient irradiation dose of ultrasonic waves at a specific area of the object can be avoided.

Further, because the ultrasonic irradiator 3a is arranged so as to be freely moved along the plane area 42a of the rigid material 42, or to be freely tilted with respect to the plane area 42a, in the ultrasonic irradiation apparatus, unevenness of the sonic field caused by an uneven arrangement of the ultrasonic transducers 1a and 1b is averaged. Therefore, a displacement range of movement or tilting of the ultrasonic irradiator 3a is preferably of about the same distance as an interval between the ultrasonic transducers 1a and 1b.

In the ultrasonic irradiation apparatus, a soft material 43 is arranged along one plane of the planar bag 41. The ultrasonic irradiation apparatus can make contact, via the soft material 43, with an object having three-dimensionally curved surfaces such as the living body 6. Therefore, the ultrasonic irradiator can be arranged inside of the planar bag 41 so that the plurality of ultrasonic transducers is installed on a surface of the rigid sheet, as shown by 3a in FIG. 13.

Next, a structure by which the ultrasonic irradiator 3a is freely movable along the plane area 42a of the rigid material 42, or is freely tilted with respect to the planar area 42a, shall be explained.

Figure 14:
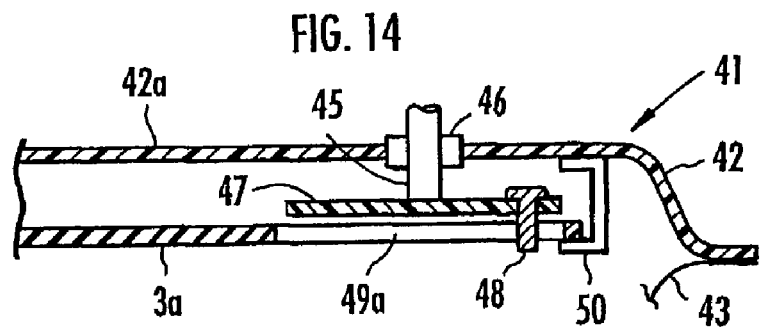
FIG. 14 is a cross sectional figure showing an example of a structure for movement of an ultrasonic irradiator, in the ultrasonic irradiation apparatus depicted in FIG. 13.

In the case where the ultrasonic irradiator 3a is arranged so as to be freely moved along the plane area 42a of the rigid material 42, the ultrasonic irradiator 3a is suspended from the rigid material 42 by at least three support members 45, so as to be flexibly movable, as shown in FIG. 14.

Then, one support member 45 is connected, via a watertight bearing 46, to the rotating axis of a motor (not shown) which is arranged outside of the planar bag 41, so as to be freely rotated. A disc 47 is installed at an end of the support member 45, and a pin 48, which is arranged at the peripheral portion so as to be project vertically downward, is inserted into a long narrow opening 49a provided in the ultrasonic irradiator 3a. The opening 49a has a length corresponding to a diameter of the disc 47.

As a result of this structure, because the pin 48 engages with the opening 49a and moves the ultrasonic irradiator 3a in accordance with rotation of the support member 45, the ultrasonic irradiator 3a is freely moved along the planar area 42a of the rigid material 42.

In this case, a guide member 50 may be arranged at a right-hand location inside of the rigid material 42, for supporting an edge portion of the ultrasonic irradiator 3a, in a direction crossing at a right angle with respect to the length direction of the opening 49a. When a guide member 50 is provided also at the other left-hand side of the rigid material 42, the ultrasonic irradiator 3a reciprocates in a direction crossing at a right angle to the length direction of the opening 49a because movement in the length direction of the opening 49a is restricted by the guide member 50.

Figure 15:
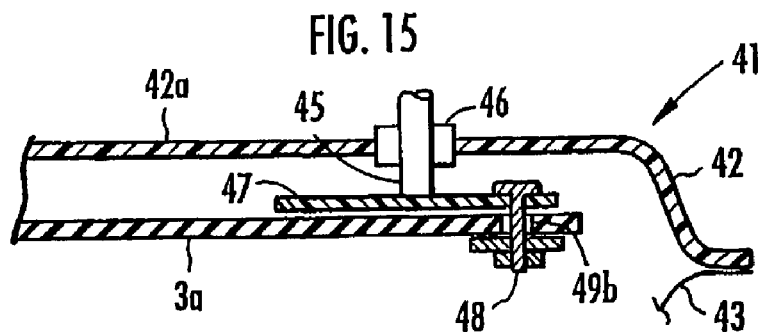
FIG. 15 is a cross sectional figure showing another example of a structure for movement of an ultrasonic irradiator, in the ultrasonic irradiation apparatus depicted in FIG. 13.

Further, an insertion hole 49b into which the pin 48 is inserted may be provided as shown in FIG. 15, in place of the long narrow opening 49a. In this case, because the pin 48 is engaged in the insertion hole 49b and, in accordance with rotation of the support member 45a, is driven to move the ultrasonic irradiator 3a, the ultrasonic irradiator 3a undergoes a circular motion along the periphery of the disc 47.

Next, a case in which the ultrasonic irradiator 3a is arranged so as to be freely tilted with respect to the planar area 42a of the rigid material 42 shall be explained. The ultrasonic irradiator 3a is supported approximately at the center of a side wall of the rigid material 42 by a freely rotatable support member 51, as depicted in FIG. 16.

On the right-hand side wall of the rigid material 42, a rotating axle 52 is installed and connected, via a watertight bearing (not shown) to a motor (also not shown) which is arranged on the outside of the planar bag 41. A disc 53 is installed at one end of the rotating axix 52, and a pin 54, arranged at the peripheral edge portion of the disc 53 and projecting frontward, is inserted into a long narrow slit 55 arranged in a side plane of the ultrasonic irradiator 3a. The slit 55 has a length corresponding to a diameter of the disc 53.

Based on this structure, because the pin 54 is engaged with the slit 55 and is driven to move an end of the ultrasonic irradiator 3a where the slit 55 has been provided, in accordance with rotation of the rotating axis 52, the ultrasonic irradiator 3a moves up and down in a range corresponding to the diameter of the disc 53. Then, because the ultrasonic irradiator 3a has been supported on a side wall of the rigid material 42 by the support member 51, which is freely rotatable, the ultrasonic irradiator 3a can be freely tilted with respect to the plane area 42a of the rigid material 42, with the support member 51 serving as an axis.

Figure 16:
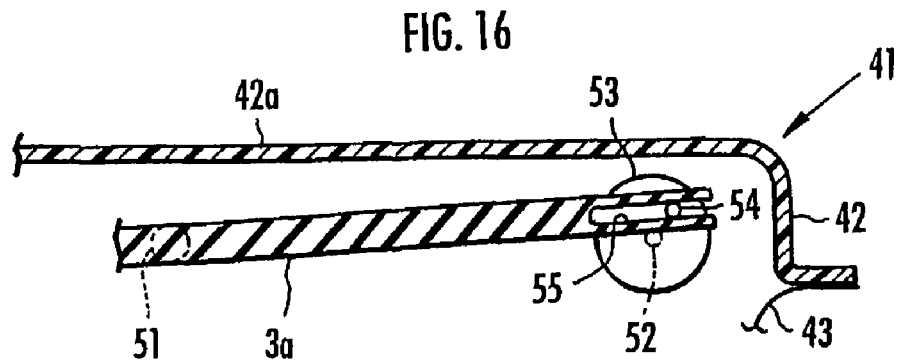
FIG. 16 is a cross sectional figure showing an example of a structure for tilting an ultrasonic irradiator, in the ultrasonic irradiation apparatus depicted in FIG. 13.

The ultrasonic irradiator 3a may be driven by a linear motor, a water-powered piston, an electromagnetic moving solenoid or water-powered motor, etc., instead of using the structure shown in FIG. 14 through FIG. 16. Thereby, the ultrasonic irradiator 3a may be arranged so as to be freely moved along the plane area 42a of the rigid material 42, or to be freely tilted with respect to the plane area 42a of the rigid material 42.

Figure 17:
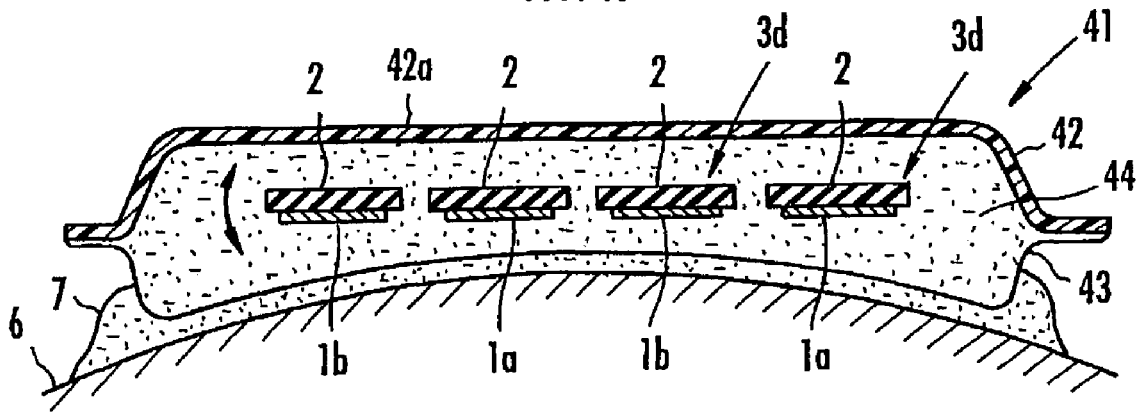
FIG. 17 is a cross sectional figure showing another example of an ultrasonic irradiation apparatus, according to the fifth embodiment of the present invention.

Further, in the case where the ultrasonic irradiator 3a is arranged so as to be freely tilted with respect to the plane area 42a of the rigid material 42, it is preferable to use an ultrasonic irradiator 3d in which the ultrasonic irradiator 3a is divided into a unit of subdivided rows, each row having a plurality of ultrasonic transducers 1a and 1b as shown in FIG. 17. In the ultrasonic irradiator 3d, the tilting angle with respect to the plane area 42a of the rigid material 42 can be made larger than that of the ultrasonic irradiator 3a, and thereby a change of position, where the ultrasonic waves irradiated from the ultrasonic transducers 1a and 1b toward the object overlap within the object, can be made larger.

In this case, the same structures 52, 53, 54 as shown in FIG. 16 can be provided for the ultrasonic irradiator 3d, located at a right-hand side of the planar bag 41. An end of an ultrasonic irradiator row 3d and an edge of another ultrasonic irradiator row 3d are connected by a connection member 56. Thereby, in accordance with tilting of the ultrasonic irradiator row 3d, which is engaged with the slit 55, the pin 54 arranged in the disc 53 can drive the other ultrasonic irradiator rows 3d simultaneously, to tilt them with respect to the plane area 42a of the rigid material 42.

Figure 18:
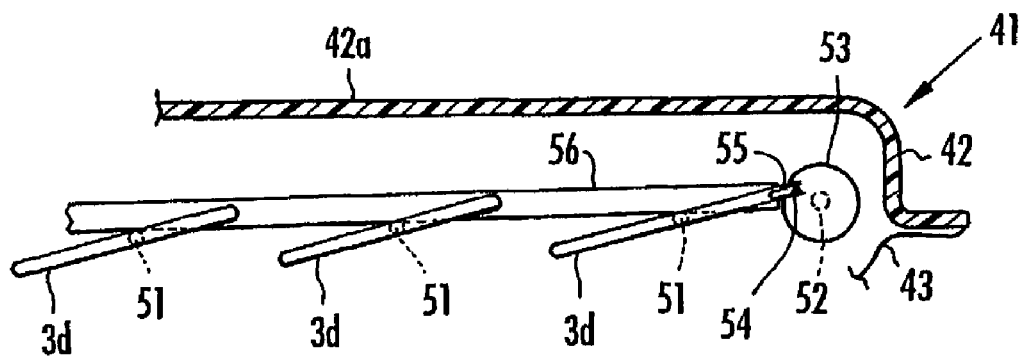
FIG. 18 is a cross sectional figure showing an example of a structure for tilting an ultrasonic irradiator, in the ultrasonic irradiation apparatus depicted in FIG. 17.

In FIG. 14 to FIG. 16, and in FIG. 18, the ultrasonic transducers 1a and 1b have not been shown for simplicity in illustration.

In the ultrasonic irradiation apparatus of the present embodiment, an plane of the planar bag 41, which is opposed to the living body 6, may be composed of a flexible material instead of the rigid material 42. It is preferable that the flexible material has a fine flexibility in one direction, but, when deformed in one direction, it becomes difficult to be deformed in a direction transverse to the deformation.

Figure 19:
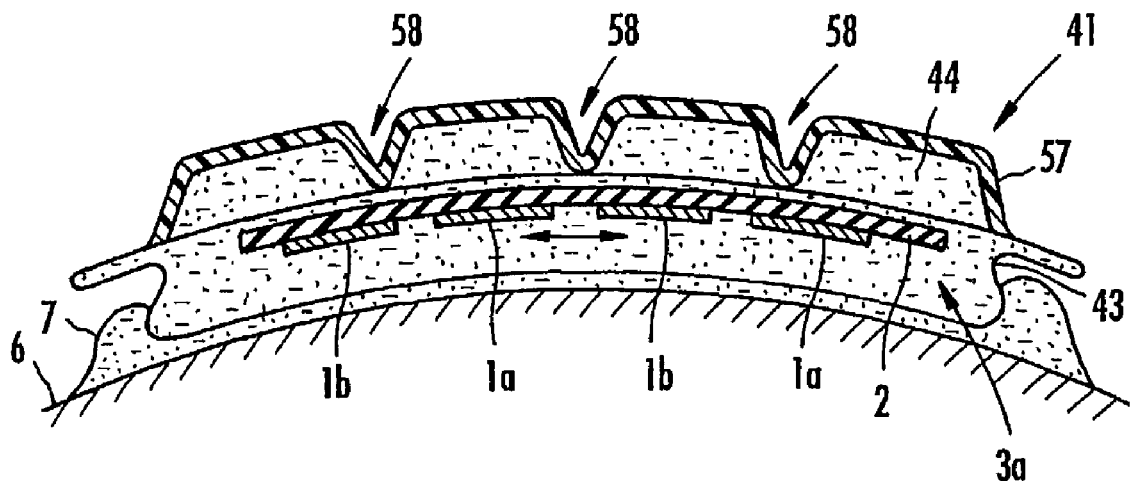
FIG. 19 is a cross sectional figure showing still another example of an ultrasonic irradiation apparatus, according to the fifth embodiment of the present invention.

Therefore, when using a flexible material 57 being fairly hard, instead of the rigid material 42, the flexible material 57 is slightly hard and is bent so as to form waves, wherein the bent portions are constructed of linear recesses 58, as depicted in FIG. 19. The top upper open portions of the linear recesses 58 can be deformed apart, and thereby the planar bag 41 also is deformed in a direction transverse to the linear recesses 58. In order to conform to curved surfaces of a living body, an output window composed of the soft material 43 is deformed in the direction of the linear recesses 58. In this case, the range at which the output window composed of the soft material 43 becomes deformed is smaller, and the thickness of the fluidic material 44 may also be smaller and lighter than in the case of FIG. 17.

Thus, the planar bag 41 can be deformed three-dimensionally, and the ultrasonic transducers 1a and 1b installed inside of the ultrasonic irradiator 3a can be arranged to conform to the three-dimensionally curved surfaces of the living body 6.

In the structure shown in FIG. 19, it is preferable that the irradiator 3a be freely movable underneath the recesses and in parallel to the living body 6, as shown by the arrow, in order to change its position for averaging, wherein the ultrasonic waves emitted from the ultrasonic transducers 1a and 1b toward the object overlap within the object, and are uneven due to the sonic field, based on the arrangement of the ultrasonic transducers 1a and 1b. For this purpose, a magnetic material can be mixed into or attached to the flexible sheet 2 of the ultrasonic irradiator 3a, and magnets can be attached at the bottom of the linear recesses 58, to keep them close while moving.

In the ultrasonic irradiation apparatus of the present embodiment, for the fluidic material 44 contained in the planar bag 41, the same fluidic material as the fluidic material 32 contained in the planar bag 31 shown in FIG. 11, composed of a heatable and/or refrigeratable high specific heat material, can be used. Therefore, in the ultrasonic irradiation apparatus, the effectiveness of irradiating an object with ultrasonic waves can be enhanced, or the feeling of the object when the object is a human can be improved, by using a fluidic material 42 that has been previously heated by, e.g., a microwave oven or cooled by an electric refrigerator.

In the ultrasonic irradiation apparatus, instead of the ultrasonic irradiator 3a, the ultrasonic irradiator 3b shown in FIG. 4 through FIG. 7, or the ultrasonic irradiator 3c shown in FIG. 8, can be used.

Figure 20:
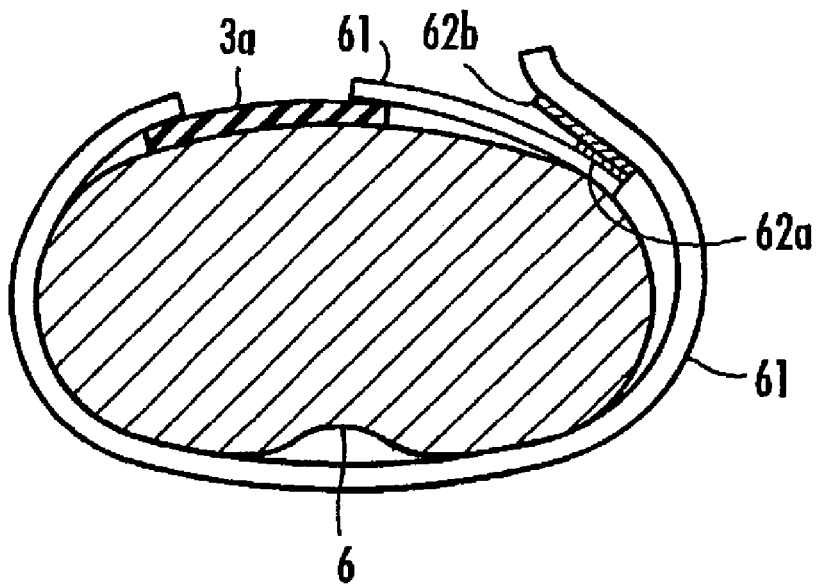
FIG. 20 is a cross sectional figure showing an example of an ultrasonic irradiation apparatus, according to a sixth embodiment of the present invention.
Figure 20:
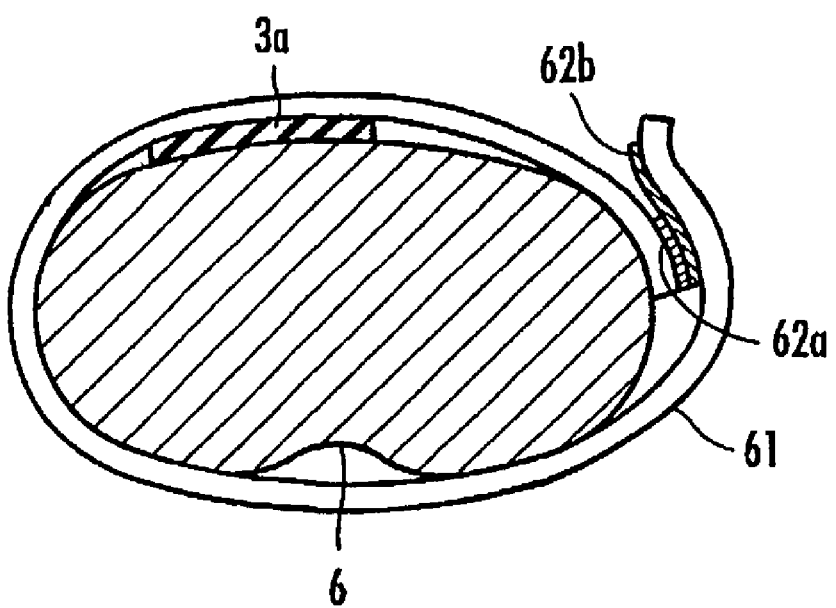
Figure 21:
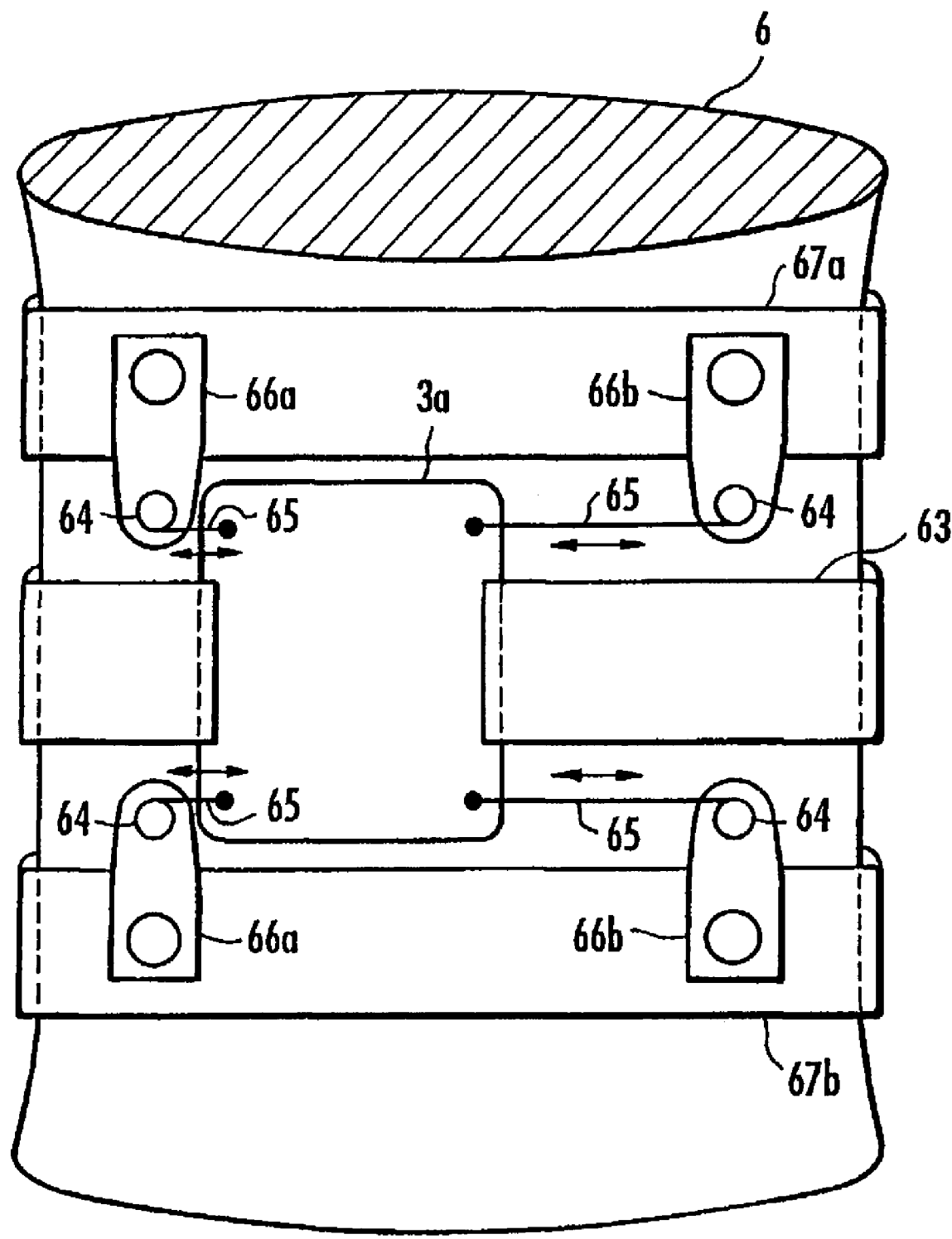
FIG. 21 is a cross sectional figure showing another example of an ultrasonic irradiation apparatus, according to the sixth embodiment of the present invention.

Next, referring to FIG. 20 and FIG. 21, an ultrasonic irradiation apparatus according to the sixth embodiment of the present invention shall be explained. The ultrasonic transducers 1a and 1b are not shown in FIG. 20 and FIG. 21, for simplicity of illustration.

The ultrasonic irradiation apparatus has a band holding member 61, arranged so that the ultrasonic irradiator 3a is easily installed, via the band holding member 61, on a region of the living body 6, such as the abdominal region or thigh, as depicted in FIG. 20(a) or FIG. 20(b). The band holding member 61 is joined to a periphery of the ultrasonic irradiator 3a, wherein the band holding member 61 is capable of being wound around the living body 6, and is tightly fixed at an appropriate position on the body by a pair of plane fasteners 62a and 62b, as depicted in FIG. 20(a).

The band holding member 61 can be arranged so as to cover the ultrasonic irradiator 3a, as depicted in FIG. 20(b). In this case, the ultrasonic irradiator 3a may be integrally fixed to the band holding member 61, or may be arranged so as to be optionally detached from the band holding member 61 by a pair of plane fasteners (not shown). Further, the ultrasonic irradiator 3a can simply be held in the band member 61 merely by friction between the band holding member 61 and itself, without having any means for fixing the ultrasonic irradiator 3a to the band holding member 61.

Because the ultrasonic irradiator 3a is fitted to the living body 6 via the band holding member 61 in the ultrasonic irradiation apparatus, the band holding member 61 greatly assists in reducing the load on an operator.

Further, it is preferable that the ultrasonic irradiator 3a be arranged so as to contact the living body 6 at the side of the flexible sheet 2, as depicted in FIG. 3. Further, the ultrasonic irradiator 3a can be arranged to have a protective layer on the non-output side thereof, and further, a layer of a material such as a fluorocarbon, having a small coefficient of friction, can be coated on the surface. Thereby, the ultrasonic irradiator 3a is arranged to be able to slide against the band holding member 61 while the ultrasonic irradiator 3a is arranged in contact with the living body 6 via the fluidic material layer 7, and is able to slide against the living body 6 as well. Therefore, the ultrasonic irradiator 3a can be moved along the living body 6 while positioned in an intervening manner between the band installation member 61 and the living body 6.

Further, the ultrasonic irradiation apparatus preferably has the structure shown in FIG. 21, so as to be freely movable along the living body 6 without being subject to friction of the band holding member 61, namely, being positioned so as not to intervene between the band and the living body 6.

The ultrasonic irradiation apparatus depicted in FIG. 21 is joined to an edge of the ultrasonic irradiator 3a without being covered by the band holding member 61. Rather, a band holding member 63 is provided, which is to be wound around the living body 6, and winding devices 66a and 66b are provided that wind strings 65 connected to the ultrasonic irradiator 3a by means of pulleys 64 driven by a motor (not shown), while additional band holding members 67a and 67b are provided to be wound around the living body 6, for fixing the overall assembly. Each of the band members 67a and 67b has a pair of plane fasteners (not shown) at an edge thereof, and can be tightly fixed to the living body 6 at an appropriate position by means of such plane fasteners.

In the ultrasonic irradiation apparatus depicted in FIG. 21, the ultrasonic irradiation apparatus 3a can be reciprocated along surfaces of the living body 6, in the length direction of the band holding member 63, by using a jelly as a lubricant, and by alternatively driving the winding devices 66a and 66b while the ultrasonic irradiation apparatus is fitted to the living body 6 by the band holding members 63, 67a and 67b.

In the ultrasonic irradiation apparatus shown in FIG. 21, the ultrasonic irradiation apparatus 3a is freely reciprocated along the length direction of the band installation member 63. However, it may also be arranged so as to be freely reciprocated in the width direction of the band installation member 63.

In the ultrasonic irradiation apparatus, it is preferable that the band holding members 61, 63, 67a and 67b be composed of a flexible material capable of absorbing or dissipating sweat. As this material, for example, a belt composed of fabric or textile, or a fiber net, may be utilized.

Further, in the ultrasonic irradiation apparatus of present embodiment, the ultrasonic irradiator 3b shown in FIG. 4 through FIG. 7, the ultrasonic irradiator 3c shown in FIG. 8, or the planar bag 41 having at least one flexible plane, as shown in FIG. 13 through FIG. 19, can be used instead of the ultrasonic irradiator 3a.

INDUSTRIAL APPLICABILITY

The present invention is applicable, e.g., for use in irradiating a living body with ultrasonic waves for lipolysis within the living body, and for acceleration of the bloodstream and the infiltration of medicines.

The invention claimed is:

1. An ultrasonic irradiation apparatus comprising:
an ultrasonic irradiator having a living body contact sheet member being ultrasonically conductive and being flexible and/or elastic; and
a plurality of ultrasonic transducers arranged in a planar pattern on one plane of said living body contact sheet member, wherein the transducer-arranged plane is apart from a contact plane of said living body,
wherein said ultrasonic irradiator has at least one of an air backing layer and a sonic absorbing layer disposed on a back side area of said ultrasonic transducers,
wherein said air backing layer and said sonic absorbing layer are substantially non-ultrasonically conductive and formed from materials different from the material constituting said living body contact sheet member, and
wherein said ultrasonic irradiator has a detachable soft material layer on a contact plane of the living body contact sheet member, wherein the soft material layer can be heated or cooled and attached on the living body contact sheet member.

2. The ultrasonic irradiation apparatus according to claim 1, wherein said plurality of ultrasonic transducers have ground electrodes disposed on a back side of the living body contact sheet member, all of said ground electrodes being mutually connected to each other and to a ground electric potential, and opposed drive electrodes, wherein plural drive electrodes are connected together in one or more groups mutually to each other and to a driving electric potential.

3. The ultrasonic irradiation apparatus according to claim 1, wherein the plurality of ultrasonic transducers are composed of a plurality of drive electrodes arranged on one surface of a flexible piezoelectric sheet member and a plurality of opposed electrodes arranged on the other surface facing each other.

4. The ultrasonic irradiation apparatus according to claim 1, wherein the living body contact sheet member comprises a flexible planar bag containing a fluidic material being ultrasonically conductive, and the bag further has a pump for periodically changing a volume of the contained fluidic material and a tube for supplying or discharging the fluidic material.

5. An ultrasonic irradiation apparatus comprising:
an ultrasonic irradiator having a living body contact sheet member being ultrasonically conductive and being flexible and/or elastic; and
a plurality of ultrasonic transducers arranged in a planar pattern on one plane of said living body contact sheet member, wherein the transducer-arranged plane is apart from a contact plane of said living body,
wherein said ultrasonic irradiator has at least one of an air backing layer and a sonic absorbing layer disposed on a back side area of said ultrasonic transducers, wherein said air backing layer and said sonic absorbing layer are substantially non-ultrasonically conductive and formed from materials different from the material constituting said living body contact sheet member, and wherein said ultrasonic irradiator comprises an impedance adjusting means for allocating an output distribution over the plurality of ultrasonic transducers, so that a sonic intensity of each of said ultrasonic transducers assumes a predetermined respective intensity ratio while said ultrasonic irradiator is flexibly deformed, and wherein said impedance adjusting means is arranged in parallel to each transducer or parallel to a predetermined number of said transducers.

6. An ultrasonic irradiation apparatus comprising:

an ultrasonic irradiator having a living body contact sheet member being ultrasonically conductive and being flexible and/or elastic; and a plurality of ultrasonic transducers arranged in a planar pattern on one plane of said living body contact sheet member, wherein the transducer-arranged plane is apart from a contact plane of said living body, wherein said ultrasonic irradiator has at least one of an air backing layer and a sonic absorbing layer disposed on a back side area of said ultrasonic transducers, wherein said air backing layer and said sonic absorbing layer are substantially non-ultrasonically conductive and formed from materials different from the material constituting said living body contact sheet member, and wherein said ultrasonic irradiator comprises an adjusting inductance, approximately resonant to each ultrasonic transducer, so that a sonic intensity of each of said ultrasonic transducers assumes a predetermined respective intensity ratio while said ultrasonic irradiator is flexibly deformed, and wherein said adjusting inductance is arranged in series with each transducer or in series with a predetermined number of transducers.

7. An ultrasonic irradiation apparatus comprising:

an ultrasonic irradiator comprising a flexible and/or elastic net member;

a plurality of ultrasonic transducers installed on the net member and arranged in a planar pattern, wherein each of said ultrasonic transducers is held by said net member only on a non-ultrasonically transmitting back portion and/or a side portion thereof, which is distinct from an ultrasonically transmitting face portion of each of said ultrasonic transducers, wherein said net member is constructed by one of flexible and/or elastic fiber strings, rubber strings, metallic chains, hard plastic chains, coiled springs, and rigid rods that are linked together at their ends so as to be freely deformable and rotatable, and wherein said ultrasonic irradiator has a detachable soft material layer on a contact plane of the living body contact net member, wherein the soft material layer can be heated or cooled and attached on the living body contact net member.

8. The ultrasonic irradiation apparatus according to claim 7, wherein said plurality of ultrasonic transducers have ground electrodes disposed on a back side of the living body contact net member, all of said ground electrodes being mutually connected to each other and to a ground electric potential, and opposed drive electrodes, wherein plural drive electrodes are connected together in one or more groups mutually to each other and to a driving electric potential.

9. The ultrasonic irradiation apparatus according to claim 7, wherein the plurality of ultrasonic transducers are composed of a plurality of drive electrodes arranged on one surface of a flexible piezoelectric sheet member and a plurality of opposed electrodes arranged on the other surface facing each other.

10. The ultrasonic irradiation apparatus according to claim 7, wherein the living body contact net member comprises a flexible planar bag containing a fluidic material being ultrasonically conductive, and the bag further has a pump for periodically changing a volume of the contained fluidic material and a tube for supplying or discharging the fluidic material.

11. An ultrasonic irradiation apparatus comprising:

an ultrasonic irradiator comprising a flexible and/or elastic net member;

a plurality of ultrasonic transducers installed on the net member and arranged in a planar pattern, wherein each of said ultrasonic transducers is held by said net member only on a non-ultrasonically transmitting back portion and/or a side portion thereof, which is distinct from an ultrasonically transmitting face portion of each of said ultrasonic transducers, wherein said net member is constructed by one of flexible and/or elastic fiber strings, rubber strings, metallic chains, hard plastic chains, coiled springs, and rigid rods that are linked together at their ends so as to be freely deformable and rotatable, and wherein said ultrasonic irradiator comprises an impedance adjusting means for allocating an output distribution over the plurality of ultrasonic transducers, so that a sonic intensity of each of said ultrasonic transducers assumes a predetermined respective intensity ratio while said ultrasonic irradiator is flexibly deformed, and wherein said impedance adjusting means is arranged in parallel to each transducer or parallel to a predetermined number of said transducers.

12. An ultrasonic irradiation apparatus comprising:

an ultrasonic irradiator comprising a flexible and/or elastic net member;

a plurality of ultrasonic transducers installed on the net member and arranged in a planar pattern, wherein each of said ultrasonic transducers is held by said net member only on a non-ultrasonically transmitting back portion and/or a side portion thereof, which is distinct from an ultrasonically transmitting face portion of each of said ultrasonic transducers, wherein said net member is constructed by one of flexible and/or elastic fiber strings, rubber strings, metallic chains, hard plastic chains, coiled springs, and rigid rods that are linked together at their ends so as to be freely deformable and rotatable, and wherein said ultrasonic irradiator comprises an adjusting inductance, approximately resonant to each ultrasonic transducer, so that a sonic intensity of each of said ultrasonic transducers assumes a predetermined respective intensity ratio while said ultrasonic irradiator is flexibly deformed, and wherein said adjusting inductance is arranged in series with each transducer or in series with a predetermined number of transducers.

* * * * *